United States Patent
Bishop et al.

(10) Patent No.: US 11,801,253 B2
(45) Date of Patent: Oct. 31, 2023

(54) METHOD OF SAFELY AND EFFECTIVELY TREATING AND PREVENTING SECONDARY HYPERPARATHYROIDISM IN CHRONIC KIDNEY DISEASE

(71) Applicant: OPKO RENAL, LLC, Miami, FL (US)

(72) Inventors: Charles W. Bishop, Miami Beach, FL (US); Eric J. Messner, Lake Forest, IL (US)

(73) Assignee: OPKO RENAL, LLC, Miami, FL (US)

( * ) Notice: Subject to any disclaimer, the term of this patent is extended or adjusted under 35 U.S.C. 154(b) by 865 days.

(21) Appl. No.: 15/720,830

(22) Filed: Sep. 29, 2017

(65) Prior Publication Data

US 2018/0021355 A1 Jan. 25, 2018

Related U.S. Application Data

(63) Continuation of application No. 14/291,666, filed on May 30, 2014, now abandoned, which is a continuation of application No. 12/597,234, filed as application No. PCT/US2008/061594 on Apr. 25, 2008, now abandoned.

(60) Provisional application No. 60/913,850, filed on Apr. 25, 2007.

(51) Int. Cl.
- A61K 31/593 (2006.01)
- A61K 31/59 (2006.01)
- A61K 31/592 (2006.01)
- A61K 45/06 (2006.01)

(52) U.S. Cl.
CPC .......... *A61K 31/593* (2013.01); *A61K 31/59* (2013.01); *A61K 31/592* (2013.01); *A61K 45/06* (2013.01)

(58) Field of Classification Search
CPC .......... E02D 17/18; E02F 9/20; E02F 9/2054; E02F 9/26; E02F 9/261; G06Q 10/06313; G06Q 10/0633; G06Q 50/08
USPC ........................................................ 514/167
See application file for complete search history.

(56) References Cited

U.S. PATENT DOCUMENTS

| | | |
|---|---|---|
| 3,565,924 A | 2/1971 | DeLuca et al. |
| 3,833,622 A | 9/1974 | Babcock et al. |
| 3,880,894 A | 4/1975 | De Luca et al. |
| 3,974,272 A * | 8/1976 | Polli ............ A61K 9/0095 424/78.12 |
| 4,004,003 A | 1/1977 | Babcock et al. |
| 4,230,701 A | 10/1980 | Holick et al. |
| 4,335,120 A | 6/1982 | Holick et al. |
| 4,555,364 A | 11/1985 | DeLuca et al. |
| 4,668,517 A | 5/1987 | Weber et al. |
| 4,684,524 A | 8/1987 | Eckenhoff et al. |
| 4,695,591 A | 9/1987 | Hanna et al. |
| 4,721,613 A | 1/1988 | Urquhart et al. |
| 4,729,895 A | 3/1988 | Makino et al. |
| 4,755,544 A | 7/1988 | Makino et al. |
| 4,997,824 A | 3/1991 | Popovtzer et al. |
| 5,026,559 A | 6/1991 | Eichel et al. |
| 5,160,742 A | 11/1992 | Mazer et al. |
| 5,167,965 A * | 12/1992 | Schulz ............... A61K 9/1652 424/494 |
| 5,328,903 A | 7/1994 | Ishii et al. |
| 5,342,626 A | 8/1994 | Winston, Jr. et al. |
| 5,354,743 A | 10/1994 | Thys-Jacobs |
| 5,403,831 A | 4/1995 | DeLuca et al. |
| 5,431,917 A | 7/1995 | Yamamoto et al. |
| 5,472,712 A | 12/1995 | Oshlack et al. |
| 5,487,900 A | 1/1996 | Itoh et al. |
| 5,529,991 A | 6/1996 | Knutson et al. |
| 5,593,690 A | 1/1997 | Akiyama et al. |
| 5,602,116 A | 2/1997 | Knutson et al. |
| 5,614,513 A | 3/1997 | Knutson et al. |
| 5,622,941 A | 4/1997 | Knutson et al. |
| 5,693,615 A | 12/1997 | Stone |
| 5,707,980 A | 1/1998 | Knutson et al. |
| 5,756,123 A | 5/1998 | Yamamoto et al. |
| 5,783,215 A | 7/1998 | Arwidsson et al. |
| 5,795,882 A | 8/1998 | Bishop et al. |
| 5,861,386 A | 1/1999 | Knutson et al. |
| 5,869,473 A | 2/1999 | Knutson et al. |
| 5,958,451 A | 9/1999 | Chen |
| 6,034,075 A | 3/2000 | Thys-Jacobs |
| 6,051,567 A | 4/2000 | Abrahamson et al. |
| 6,121,469 A | 9/2000 | Norman et al. |
| 6,133,250 A | 10/2000 | Knutson et al. |
| 6,139,875 A | 10/2000 | Adams et al. |
| 6,147,064 A | 11/2000 | Knutson et al. |
| 6,150,346 A | 11/2000 | Knutson et al. |
| 6,190,591 B1 | 2/2001 | van Lengerich |
| 6,190,695 B1 | 2/2001 | Hoshino et al. |
| 6,228,849 B1 | 5/2001 | Thys-Jacobs |
| 6,242,434 B1 | 6/2001 | Bishop et al. |
| 6,265,392 B1 | 7/2001 | Abrahamson et al. |
| 6,274,169 B1 | 8/2001 | Abrahamson et al. |

(Continued)

FOREIGN PATENT DOCUMENTS

| | | |
|---|---|---|
| CA | 2241205 A1 | 7/1997 |
| EP | 0 227 836 A1 | 7/1987 |

(Continued)

OTHER PUBLICATIONS

AlfaD₃® 0.25, 0.5 or 1 microgram Capsules (Alfacalcidol, Package Leaflet, Apr. 2010).

(Continued)

*Primary Examiner* — Dominic Lazaro

(57) ABSTRACT

A method of treating and preventing secondary hyperparathyroidism in CKD by increasing or maintaining blood concentrations of both 25-hydroxyvitamin D and 1,25-dihydroxyvitamin D in a patient by administering 25-hydroxyvitamin $D_3$ with or without 25-hydroxyvitamin $D_2$ and, as necessary, 1,25-dihydroxyvitamin $D_2$ as a Vitamin D hormone replacement therapy.

26 Claims, No Drawings

(56) References Cited

U.S. PATENT DOCUMENTS

| | | |
|---|---|---|
| 6,288,849 B1 | 9/2001 | Teramoto |
| 6,340,473 B1 | 1/2002 | Tanner et al. |
| 6,342,249 B1 | 1/2002 | Wong et al. |
| 6,375,981 B1 | 4/2002 | Gilleland et al. |
| 6,376,479 B1 | 4/2002 | Knutson et al. |
| 6,380,408 B1 | 4/2002 | Posner et al. |
| 6,413,463 B1 | 7/2002 | Yamamoto et al. |
| 6,432,936 B1 | 8/2002 | DeLuca et al. |
| 6,503,893 B2* | 1/2003 | Bishop .................... A61P 35/02 514/167 |
| 6,521,608 B1 | 2/2003 | Henner et al. |
| 6,524,788 B1 | 2/2003 | Cantor |
| 6,569,463 B2 | 5/2003 | Patel et al. |
| 6,572,888 B2 | 6/2003 | Byrd |
| 6,582,727 B2 | 6/2003 | Tanner et al. |
| 6,596,314 B2 | 7/2003 | Wong et al. |
| 6,770,295 B1 | 8/2004 | Kreilgård et al. |
| 6,893,658 B1 | 5/2005 | Iida et al. |
| 6,903,083 B2* | 6/2005 | Knutson ................ A61K 31/59 514/167 |
| 6,911,217 B1 | 6/2005 | Gren et al. |
| 6,923,988 B2 | 8/2005 | Patel et al. |
| 6,929,803 B2 | 8/2005 | Wong et al. |
| 6,949,256 B2 | 9/2005 | Fonkwe et al. |
| 6,982,258 B2 | 1/2006 | Posner et al. |
| RE39,079 E | 4/2006 | Tanner et al. |
| 7,033,996 B2 | 4/2006 | Christakos |
| 7,056,655 B2 | 6/2006 | Cantor |
| 7,101,865 B2 | 9/2006 | Posner et al. |
| 7,122,530 B2 | 10/2006 | Bishop et al. |
| 7,189,843 B2 | 3/2007 | Tsai et al. |
| 7,226,932 B2 | 6/2007 | Gokhale et al. |
| 7,255,921 B2 | 8/2007 | Kamaguchi et al. |
| 7,422,758 B2 | 9/2008 | Block et al. |
| 7,632,518 B2 | 12/2009 | Tritsch et al. |
| 7,807,194 B2 | 10/2010 | Modliszewski et al. |
| 7,816,341 B2 | 10/2010 | Sewall et al. |
| 7,846,475 B2 | 12/2010 | Shiraishi et al. |
| 8,088,410 B2 | 1/2012 | Tritsch et al. |
| 8,101,203 B2 | 1/2012 | Cao |
| 8,101,204 B2 | 1/2012 | Cao |
| 8,142,811 B2 | 3/2012 | Oshlack et al. |
| 8,207,149 B2 | 6/2012 | Tabash et al. |
| 8,231,896 B2 | 7/2012 | Tanner et al. |
| 8,268,352 B2 | 9/2012 | Vaya et al. |
| 8,293,270 B2 | 10/2012 | Sukuru |
| 8,361,488 B2 | 1/2013 | Bishop et al. |
| 8,377,470 B2 | 2/2013 | Tanner et al. |
| 8,426,391 B2 | 4/2013 | Bishop et al. |
| 8,759,328 B2 | 6/2014 | Deluca et al. |
| 8,778,373 B2 | 7/2014 | Bishop et al. |
| 8,906,410 B2 | 12/2014 | Bishop et al. |
| 8,992,971 B2 | 3/2015 | Yang |
| 9,017,720 B2 | 4/2015 | Andersen et al. |
| 2001/0028896 A1 | 10/2001 | Byrd |
| 2001/0036472 A1 | 11/2001 | Wong et al. |
| 2002/0018810 A1 | 2/2002 | Oshlack et al. |
| 2002/0031798 A1 | 3/2002 | Anazawa et al. |
| 2002/0081331 A1 | 6/2002 | Tanner et al. |
| 2002/0128240 A1 | 9/2002 | Mazess |
| 2002/0155154 A1 | 10/2002 | Wong et al. |
| 2002/0183288 A1* | 12/2002 | Mazess ................ A61K 31/565 514/167 |
| 2003/0129194 A1 | 7/2003 | Mazess et al. |
| 2003/0138482 A1 | 7/2003 | Fonkwe et al. |
| 2003/0157560 A1 | 8/2003 | Cantor |
| 2004/0043971 A1 | 3/2004 | Mazess et al. |
| 2004/0101554 A1 | 5/2004 | Kirschner et al. |
| 2005/0019374 A1 | 1/2005 | Modliszewski et al. |
| 2005/0037064 A1 | 2/2005 | Basquin et al. |
| 2005/0069579 A1 | 3/2005 | Kamaguchi et al. |
| 2005/0101576 A1 | 5/2005 | Whitehouse et al. |
| 2005/0106233 A1 | 5/2005 | Andersen et al. |
| 2005/0124591 A1 | 6/2005 | Tian et al. |
| 2005/0143358 A1 | 6/2005 | DeLuca et al. |
| 2005/0148557 A1 | 7/2005 | Tian et al. |
| 2005/0148558 A1 | 7/2005 | Knutson et al. |
| 2005/0186268 A1 | 8/2005 | Hoshi et al. |
| 2005/0287213 A1 | 12/2005 | Wong et al. |
| 2006/0009425 A1 | 1/2006 | Delgado-Herrera et al. |
| 2006/0019933 A1 | 1/2006 | Boardman et al. |
| 2006/0029660 A1 | 2/2006 | Fonkwe et al. |
| 2006/0034937 A1 | 2/2006 | Patel |
| 2006/0193877 A1 | 8/2006 | Tengler et al. |
| 2006/0210610 A1 | 9/2006 | Davidson et al. |
| 2006/0223119 A1 | 10/2006 | Cantor |
| 2006/0228808 A1 | 10/2006 | Clarke et al. |
| 2006/0257481 A1 | 11/2006 | Gurney et al. |
| 2007/0026067 A1 | 2/2007 | Yam et al. |
| 2007/0122477 A1 | 5/2007 | Bishop et al. |
| 2007/0190146 A1 | 8/2007 | Roger et al. |
| 2008/0134937 A1 | 6/2008 | Yang |
| 2008/0317764 A1 | 12/2008 | Huber et al. |
| 2009/0137536 A1 | 5/2009 | Mazess et al. |
| 2009/0176748 A1 | 7/2009 | Tabash et al. |
| 2009/0311316 A1 | 12/2009 | Bishop et al. |
| 2010/0144684 A1 | 6/2010 | Bishop |
| 2011/0105444 A1 | 5/2011 | Deluca et al. |
| 2011/0182986 A1 | 7/2011 | Speirs et al. |
| 2011/0300210 A1 | 12/2011 | Swanson et al. |
| 2014/0088202 A1 | 3/2014 | Cade et al. |
| 2014/0248400 A1 | 9/2014 | Phonchareon et al. |
| 2014/0274977 A1 | 9/2014 | Bishop et al. |
| 2015/0119472 A1 | 4/2015 | Shuai et al. |
| 2015/0119473 A1 | 4/2015 | Shuai et al. |

FOREIGN PATENT DOCUMENTS

| | | |
|---|---|---|
| EP | 0 508 756 A1 | 10/1992 |
| EP | 0 387 808 B1 | 5/1993 |
| EP | 0629405 A1 | 12/1994 |
| EP | 1208843 A1 | 5/2002 |
| EP | 1 165 061 B1 | 10/2005 |
| EP | 2 148 661 B1 | 12/2012 |
| JP | 08-92098 A | 9/1973 |
| JP | 58-032823 | 2/1983 |
| JP | 04-208225 A | 7/1992 |
| JP | H04288016 A | 10/1992 |
| JP | 07-242550 A | 9/1995 |
| JP | 08-092098 A | 4/1996 |
| JP | 10-158171 A | 6/1998 |
| JP | 2004-175750 A | 6/2004 |
| JP | 2005-513419 A | 5/2005 |
| WO | WO-91/012807 A1 | 9/1991 |
| WO | WO-91/016899 A1 | 11/1991 |
| WO | WO-94/000128 A1 | 1/1994 |
| WO | WO-96/000074 A1 | 1/1996 |
| WO | WO-96/001621 A1 | 1/1996 |
| WO | WO-96/031215 A1 | 10/1996 |
| WO | WO-97/011053 A1 | 3/1997 |
| WO | WO-98/018610 A1 | 5/1998 |
| WO | WO-99/011272 A1 | 3/1999 |
| WO | WO-00/021504 A1 | 4/2000 |
| WO | WO-00/035419 A2 | 6/2000 |
| WO | WO-00/061123 A2 | 10/2000 |
| WO | WO-01/037808 A1 | 5/2001 |
| WO | WO-03/039521 A1 | 5/2003 |
| WO | WO-03/039572 A1 | 5/2003 |
| WO | WO-03/047595 A1 | 6/2003 |
| WO | WO-03/088976 A1 | 10/2003 |
| WO | WO-2004/028515 A1 | 4/2004 |
| WO | WO-2004/058235 A2 | 7/2004 |
| WO | WO-2004/080467 A2 | 9/2004 |
| WO | WO-2004/101554 A1 | 11/2004 |
| WO | WO-2004/110391 A2 | 12/2004 |
| WO | WO-2005/011652 A2 | 2/2005 |
| WO | WO-2005/123120 A1 | 12/2005 |
| WO | WO-2006/052452 A1 | 5/2006 |
| WO | WO-2006/059180 A2 | 6/2006 |
| WO | WO-2006/113505 A2 | 10/2006 |
| WO | WO-2007/039193 A1 | 4/2007 |
| WO | WO-2007/039569 A2 | 4/2007 |
| WO | WO-2007/047327 A2 | 4/2007 |
| WO | WO-2007/050724 A2 | 5/2007 |

(56) References Cited

FOREIGN PATENT DOCUMENTS

| WO | WO-2007/050975 A2 | 5/2007 |
|---|---|---|
| WO | WO-2007/053608 A2 | 5/2007 |
| WO | WO-2007/068287 A1 | 6/2007 |
| WO | WO-2007/092755 A2 | 8/2007 |
| WO | WO-2007/146004 A1 | 12/2007 |
| WO | WO-2008/008608 A2 | 1/2008 |
| WO | WO-2008/097646 A1 | 8/2008 |
| WO | WO-2008/134512 A1 | 11/2008 |
| WO | WO-2008/134523 A1 | 11/2008 |
| WO | WO-2009/047644 A2 | 4/2009 |
| WO | WO-2009/101132 A1 | 8/2009 |
| WO | WO-2009/101137 A1 | 8/2009 |
| WO | WO-2010/011906 A1 | 1/2010 |
| WO | WO-2010/034342 A1 | 4/2010 |
| WO | WO-2011/031621 A2 | 3/2011 |
| WO | WO-2011/095388 A1 | 8/2011 |
| WO | WO-2012/018329 A1 | 2/2012 |
| WO | WO-2012/076429 A1 | 6/2012 |
| WO | WO-2012/091569 A1 | 7/2012 |
| WO | WO-2012/117236 A1 | 9/2012 |
| WO | WO-2014/202754 A1 | 12/2014 |

OTHER PUBLICATIONS

Alfarol® Capsules 3µg (Package Leaflet, Mar. 2011).
Ashford, Chapter 20: Bioavailability—physicochemical and dosage form factors, pp. 314-333 in: Aulton et al. (eds.), *Aulton's Pharmaceutics. The Design and Manufacture of Medicines*, Fourth Edition, Elsevier Publishing (2013).
Hectorol® (doxercalciferol) Capsules (Label, FDA, 2010).
Zemplar® (paricalcitol) Capsules, Final Agreed Upon Label (FDA, May 5, 2009).
Sitrin et al., Comparison of vitamin D and 25-hydroxyvitamin D absorption in the rat, Am. J. Physiol., 242(4):G326-32 (1982).
Holmberg et al., Absorption of a pharmacological dose of vitamin D3 from two different lipid vehicles in man: comparison of peanut oil and a medium chain triglyceride, Biopharm. Drug Dispos., 11(9):807-15 (1990).
Hidroferol® (calcifediol): Casos de Hipercalcemia e Hipervitaminosis D, Butlletí de Farmacovigilància de Catalunya, 9(5):17-20 (2011).
K/DOQI Clinical Practice Guidelines for Bone Metabolism and Disease in Chronic Kidney Disease, National Kidney Foundation, *Am. J. Kidney Dis.*, 42 (Supplement 3):1-202 (2003).
Modern Pharmaceutics 4th ed., Marcel Dekker, Inc., New York, NY, p. 16-21 (2002).
Al-Aly, Changes in Serum 25-Hydroxyvitamin D and Plasma Intact PTH Levels Following Treatment with Ergocalciferol in Patients With CKD, Am. J. Kid. Dis., 50(1):59-68 (2007).
Alvarez et al., Vitamin D Supplementation in Pre-Dialysis Chronic Kidney Disease, *Dermato-Endocrinology*, 4(2):118-127 (2012).
Andress, Vitamin D in chronic kidney disease: a systematic role for selective vitamin D receptor activation, *Kidney Int.*, 69:33-43 (2006).
Arekat et al., Dramatic Improvement of BMD Following Vitamin D Therapy in a Bone Marrow Transplant Recipient, *J. Clin. Densitometry*, 5:267-271 (2002).
Armas et al., Vitamin $D_2$ is Much Less Effective than Vitamin $D_3$ in Humans, *J. Clin. Endocrinol. Metab.*, 89:5387-5391 (2004).
Baggiolini et al., Stereocontrolled Total Synthesis of 1α,25-Dihydroxycholecalciferol 1 and 1α,25-Dihydroxyergocalciferol, J. Org. Chem. 21: 3098-3108 (1986).
Bagnis et al., Biochemical and Hormonal Short-Term Effects of 25-hydroxyvitamin D3 in Patients on Continuous Peritoneal Dialysis, *Ital. J. Mineral Electrolyte Metab.*, 12:73-76 (1998).
Bailie et al. Comparative Review of the Pharmacokinetics of Vitamin D Analogues, *Seminars in Dialysis*, 15(5):352-357 (2000).
Baird et al., Steroid Dynamics Under Steady-State Conditions, *Recent Prog. Horm. Res.*, 25:611-664 (1969).
Barger-Lux et al., Vitamin D and Its Major Metabolites: Serum Levels After Graded Oral Dosing in Healthy Men *Osteoporosis International*, United Kingdom, 8(3):222-230 (1998).

Barreto et al., 25-Hydroxyvitamin $D_3$, the Prohormone of 1,25-Dihydroxyvitamin $D_3$, Inhibits the Proliferation of Primary Prostatic Epithelial Cells, *Cancer Epidemiol, Biomarkers & Prevention*, 9:265-270 (2000).
Beckman et al., Up-Regulation of the Intestinal 1,25-Dihydroxyvitamin D Receptor During Hypervitaminosis D: a Comparison Between Vitamin D2 and Vitamin D31, Biochemical and Biophysical Research Communications, vol. 169, No. 3, pp. 910-915 (Jun. 29, 1990).
Beer et al., Pharmacokinetics and Tolerability of a Single Dose of DN-101, a New Formulation of Calcitriol, in Patients with Cancer, *Clin. Cancer Res.*, 11:7794-7799 (2005).
Bell et al., Evidence that 1,25-Dihydroxyvitamin D3 Inhibits the Hepatic Production of 25-Hydroxyvitamin D in Man, *J. Clin. Invest.*, 74:1540-1544 (1984).
Belostotsky et al., A single high dose of ergocalciferol can be used to boost 25-hydroxyvitamin D levels in children with kidney disease, *Pediatr Nephrol*, 24:625-626 (2009).
Bianchi et al., No Difference in Intestinal Strontium Absorption After an Oral or an Intravenous 1,25(OH)2D3 Bolus in Normal Subjects, *J. Bone Miner. Res.*, 14:1789-1795 (1999).
Binkley et al., Laboratory Reporting of 25-Hydroxyvitamin D Results: Potential for Clinical Misinterpretation, *Clinical Chemistry*, 52(11);2124-2125 (2006).
Blair et al., Prevalence of vitamin D [25(OH)D] deficiency and effects of supplementation with ergocalciferol (vitamin D2) in stage 5 chronic kidney disease patients. *J.Ren Nutr.*, 18: 375-382 (2008).
Blunt et al., Biological activity of 25-hydroxycholecalciferol, a metabolite of vitamin D3, Proc. Natl. Acad. Sci. USA, 61(4):1503-6 (1968).
Bordier et al., Evolution of renal osteodystrophy: Correlation of bone histomorphometry and serum mineral and immunoreactive parathyroid hormone values before and after treatment with calcium carbonate or 25-hydroxycholecalciferol, *Kidney Int Suppl*, 2:S102-S112 (1975).
Boudville et al., Renal Function and 25-Hydroxyvitamin D Concentrations Predict Parathyroid Hormone Levels in Renal Transplant Patients, *Nephrol Dial Transplant*, 21:2621-2624 (2006).
Bouillon et al., Influence of dialysate calcium concentration and vitamin D on serum parathyroid hormone during repetitive dialysis, *Kidney Int.*, 7:422-432 (1975).
Brossard et al. Influence of Glomerular Filtration Rate on Non-(1-84) Parathyroid Hormone (PTH) Detected by Intact PTH Assays, *Clinical Chemistry*, 46(5):697-703 (2000).
Brown et al., The Vitamin D Prodrugs 1α(OH)$D_2$, 1α(OH)$D_3$ and BCI-210 Suppress PTH Secretion by Bovine Parathyroid Cells, *Nephrol Dial Transplant*, 21:644-650 (2006).
Brown et al., Vitamin D Analogues for Secondary Hyperparathyroidism, Nephrol Dial Transplant, 17[Suppl. 10]:10-19 (2002).
Buccianti et al., Effects of Calcifediol Treatment on the Progression of Renal Osteodystrophy during Continuous Ambulatory Peritoneal Dialysis, *Nephron*, 56:353-356 (1990).
Budavari (ed.), *Merck Index: an Encyclopedia of Chemicals, Drugs, and Biologicals*, 11th Edition, Merck & Co., 9927-9930 (1989).
Bulla et al., Renal bone disorders in children: therapy with vitamin D3 or 1,25-dihydroxycholecalciferol, *Proc.Eur.Dial.Transplant. Assoc.*, 16: 644-8 (1979).
Chandra et al., Cholecalciferol (vitamin D3) therapy and vitamin D insufficiency in patients with chronic kidney disease: a randomized controlled pilot study, *Endocr.Pract.*, 14: 10-7 (2008).
Chonchol et al., 25-Hydroxyvitamin D, insulin resistance, and kidney function in the Third National Health and Nutrition Examination Survey, Kidney Int., 71(2):134-9 (2007).
Claris-Appiani et al., Phosphate-Induced PTH Stimulation and Calcitriol Treatment in Children with Early Chronic Renal Insufficiency, *J. Bone Miner. Met.*, 12:S91-S97 (1994).
Coburn et al., Doxercalciferol Safely Suppresses PTH Levels in Patients with Secondary Hyperparathyroidism Associated with Chronic Kidney Disease Stages 3 and 4, *Am. J. Kidney Dis.*, 43(5):877-890 (2004).
Coburn et al., Use of active Vitamin D sterols in patients with chronic kidney disease, stages 3 and 4, Kidney Int., 63:85 pp. 549-553 (2003).

(56) References Cited

OTHER PUBLICATIONS

Coburn, An Update on Vitamin D as Related to Nephrology Practice: 2003, *Kidney International*, vol. 64, Supplement 87, pp. S125-S130 (2003).
Coburn et al., Use of Active Vitamin D Sterols in Patients with Chronic Kidney Disease, Stages 3 and 5, Kidney International, vol. 63, Supplement 85, pp. S49-S53 (2003).
Coen et al., 1,25(OH)2D3 and 25-OHD3 in the Treatment of Renal Osteodystrophy: Comparison of Combined Versus 1,25(OH)2D3 Administration Alone, *Miner. Electrolyte Metab.*, 9:19-27 (1983).
Coen et al., 25-hydroxycholecalciferol in the treatment of renal osteodystrophy in haemodialysed patients, *Int J Artificial Organs*, 2(6): 278-281 (1979).
Coen et al., 25-hydroxycholecalciferol in the treatment of renal osteodystrophy in haemodialysed patients, *Int J Artificial Organs*, 2(6): 278-81 (1979).
Cohen-Solal et al., Non-Aluminic Adynamic Bone Disease in Non-Dialyzed Uremic Patients: a New Type of Osteopathy Due to Overtreatment? *Bone*, 13:1-5 (1992).
Collet et al. Modified-Release Peroral Dosage Forms, Aulton (ed.), Pharmaceutics: the Science of Dosage Forms, Churchill Livingston, London, pp. 289-305 (2002).
Colodro et al., Effect of 25-Hydroxy-Vitamin D3 on Intestinal Absorption of Calcium in Normal Man and Patients With Renal Failure, *Metabolism*, 27(6):745-753 (1978).
Cooke et al., Vitamin D-Binding Protein (Gc-Globulin): Update 1995, *Endocrine Rev.*, 4:125-128 (1995).
Coyne et al., Paricalcitol Capsule for the Treatment of Secondary Hyperparathyroidism in Stages 3 and 4 CKD, *American Journal of Kidney Diseases*, 47(2):263-276 (2006).
Daisley-Kydd et al., Calcitriol in the Management of Secondary Hyperparathyroidism of Renal Failure, *Pharmacotherapy.*, 16:619-630 (1996).
Davies et al. The Absorption and Metabolism of Vitamin D3 from Parenteral Injection Sites', Proceedings of the Workshop on Vitamin D, 4th, Vitam. D: Basic Res. Its Clin. Appl. (1979), abstract.
DB-Pharma, Dedrogyl 15 Mg/10ML Calcifediol Oral Drops, Solution, Marketing Authorization No. 317 863.2 (2000).
DeLuca, Treatment of renal osteodystrophy with 25-hydroxycholecalciferol, *Arch Intern Med*, 126(5):896-899 (1970).
Deroisy et al., Comparison of the Short-Term Effects of Three Oral Calcium-Vitamin D Formulations and Placebo on Calcium Metabolism, *Curr. Ther. Res.*, 59:370-378 (1998).
Deville et al., Effect of Ergocalciferol Supplementation on Serum Parathyroid Hormone and Serum 25-Hydroxyvitamin D in Chronic Kidney Disease, *Nephrology*, 11:555-559 (2006).
*Dietary Reference Intakes for Calcium, Phosphorus, Magnesium, Vitamin D, and Fluoride*, Standing Committee on the Scientific Evaluation of Dietary Reference Intakes, Food and Nutrition Board, Institute of Medicine, National Academy Press, Washington DC, pp. 250-287 (1997).
*Dietary Supplement Fact Sheet: Vitamin D*, National Institutes of Health, Office of Dietary Supplements (last update: Aug. 5, 2005), retrieved from <URL: http:ods.od.nih.gov/factsheets/vitamind.asp> on Aug. 31, 2007.
*Disease and Vitamin D*, University of California Riverside, retrieved from Internet, <URL: <http://vitamind.ucr.edu/disease.html>> (last update: May 19, 1999).
Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30.
Dogan et al., Effect of depot oral cholecalciferol treatment on secondary hyperparathyroidism in stage 3 and stage 4 chronic kidney diseases patients, *Ren Fail.*, 30: 407-410 (2008).
Drueke et al., Recurrence of hyperparathyroidism from autografted parathyroid fragments in uremic patients in spite of administration of 25(OH)D3 and 1a(OH)D3. In: Vitamin D. Basic Research and its Clinical Application, (Eds. Norman AW, Schaefer K, Herrath Dv, Grigoleit HG, Coburn JW, DeLuca HF, Mawer EB, and Suda T), pp. 791-794. Willem de Gruyter, New York (1979).

Dusso et al, Metabolic Clearance Rate and Production Rate of Calcitriol in Uremia, *Kidney Int.*, 35 860-864 (1989).
Dusso et al., Extra-renal production of calcitriol in chronic renal failure, *Kidney Int.*, 34:368-375 (1988).
Dusso et al., Extrarenal Production of Calcitrol in Normal and Uremic Humans*, *Journal of Clinical Endocrinology and Metabolism*, 72(1):157-164 (1991).
Eastwood et al., Biochemical and histological effects of 1,25 dihydroxycholecalciferol (1,25-DHCC) in the osteomalacia of chronic renal failure, *J Urol Nephrol (Paris,)* 80(12): 984-985 (1974).
Eastwood et al., The contrasting effects on bone histology of vitamin D and of calcium carbonate in the osteomalacia of chronic renal failure, *Clin Sci Molec Med*, 47:23-42 (1974).
Eastwood et al., The Effect of 25-Hydroxy Vitamin D3 in the Osteomalacia of Chronic Renal Failure, *Clin. Sci. Molec. Med.*, 52:499-508 (1977).
Fernandez et al., Guidelines for Dosing of Intravenous Calcitriol in Dialysis Patients with Hyperparathyroidism, *Nephrol. Dial. Transplant.*, 11:96-101 (1996).
Fournier et al., 1-alpha-Hydroxycholecalciferol and 25-Hydroxycholecalciferol in Renal Bone Disease, *Calcified Tissues 1975: Proceedings of the 11th European Symposium on Calcified Tissues*, 226-235 (1975).
Fournier et al., Advances in Nephrology from the Necker Hospital *Adv. Nephrol Necker Hosp.* 21:237-306 (1992).
Fournier et al., Comparison of 1α-hydroxycholecalciferol and 25-hydroxycholecalciferol in the treatment of renal osteodystrophy: Greater effect of 25-hydroxycholecalciferol on bone mineralization *Kidney International* 15:196-204 (1979).
Fournier et al., Current Status of the Management of Renal Osteodystrophy *Proceedings of the European Dialysis and Transplant Association* 15:547-568 (1978).
Fournier et al., Importance of Vitamin D Repletion in Uraemia, *Nephrol Dial Transplant*, 14(4):819-823 (1999).
Fournier et al., Low doses of calcitriol or calcium carbonate for the prevention of hyperparathyroidism in predialysis patients? *Nephrol Dial Transplant* 11(7):1493-5 (1996).
Fournier et al., Present-Day Concepts in the Treatment of Chronic Renal Failure *Contrib Nephrol.* 71:64-80 (1989).
Fournier et al., Preventing renal bone disease in moderate renal failure with CaCO3 and 25 (OH) vitamin D3 Kidney International, 33(24):S178-S179 (1988).
Fournier et al., Renal Osteodystrophy in Dialysis Patients: Diagnosis and Treatment, *Artificial Organs*, 22:530-557 (1998).
Fournier et al., Renal Osteodystrophy: Pathophysiology and Treatment *Hormone Res.* 20:44-58 (1984).
Fournier et al., The Approach to the Treatment of Secondary Hyperparathyroidism in Early Renal Failure *Am. J. Nephrol* 8:170-172 (1988).
Fournier et al., Traitement vitaminique D et osteodystrophies renales: indications et modalitiés *Nephrologie* 16(2):165-190 (1995) [journal in French]—abstract only.
Fournier et al., 1α Hydroxycholecalciferol and 25 Hydroxycholecalciferol in Renal Bone Disease *Proc Eur Dial Transplant Assoc* 12:227-36 (1976).
Fournier et al., 1alpha-hydroxycholecalciferol and 25-hydroxycholecalciferol in renal bone disease, Calcif Tissue Res. 21:226-35 (1976).
Fournier et al., Prevention of secondary hyperparathyroidism in chronic renal failure before dialysis, Contrib. Nephrol., 71:64-80 (1989).
Fournier, Vitamin D: Biochemical, Chemical, and Clinical Aspects Related to Calcium Metabolism, Vitamin D: Proceedings of the Third Workshop on Vitamin D, Asilomar, Pacific Grove, CA, USA 667-669 (1977).
Friedman et al. The Role of Vitamin D in Mild to Moderate Chronic Kidney Disease, *Trends in Endocrinology & Metab,.* 13(5):189-194 (2002).
Fritsche et al., Regulation of 25-Hydroxyvitamin $D_3$-1α-Hydroxylase and Production of 1α,25-Dihydroxyvitamin $D_3$ by Human Dendritic Cells, *Blood*, 102(9):3314-3316 (2003).

(56) References Cited

OTHER PUBLICATIONS

Frohling et al., Serum 25-hydroxyvitamin D in patients with chronic renal failure on long-term treatment with high doses of vitamin D2. *Nephron* 26:116-120 (1980).
Frost et al., Histomorphometric Changes in Trabecular Bone of Renal Failure Patients Treated with Calcifediol, *Metab. Bone Dis. & Rel. Res.*, 2:285-295 (1981).
Gallagher et al., Comparison of the Histological Effect and Metabolism of 25-(OH)D and 1,25-(OH)2D in Rat Bone, p. 399-401, in: Norman, *Vitamin D: Basic Research and its Clinical Application: Proceedings of the Fourth Workshop on Vitamin D*, Berlin, West Germany, Feb. 1979.
Ghazali et al., Is low plasma 25-(OH) vitamin D a major risk factor for hyperparathyroidism and Looser's zones independent of calcitriol? *Kidney International* 55:2169-2177 (1999).
Gibson, ed., Product optimisation. *Pharmaceutical Preformulation and Formulation: a Practical Guide from Candidate Drug Selection to Commercial Dosage Form*, 295-8 (2004).
Granja et al., Studies on the Opening of Dioxanone and Acetal Templates and Application to the Synthesis of 1α,25-Dihydroxyvitamin D21, J. Org. Chem, 58 pp. 124-131 (1993).
Gómez-Alonso et al., Vitamin D Status and Secondary Hyperparathyroidism: the Importance of 25-Hydroxyvitamin D Cut-Off Levels, *Kidney International*, 63(Supp. 85):S44-S48 (2003).
Haddad et al., Acute Administration of 25-Hydroxycholecalciferol in Man, *J. Clin. Endocrinol. Metab.*, 42:284-289 (1976).
Haddad et al., Human Serum Binding Capacity and Affinity for 25-Hydroxyergocalciferol and 25-Hydroxycholecalciferol, *J. Clin. Endocrinol. Metab.*, 43:86-91 (1976).
Haddad et al., Natural and Synthetic Sources of Circulating 25-Hydroxyvitamin D in Man, *Nature*, 244:515-517 (1973).
Haddad, Plasma Vitamin D-binding Protein (Gc-Globulin): Multiple Tasks, *J. Steroid Biochem. Molec. Biol.*, 53:579-582 (1995).
Haddad, Seasonal Diminution of Vitamin D Stores in the United States: Can Darker Winters Lead to Lighter Bones? *Trends Endocrinol. Metab.*, 7:209-212 (1996).
Haddad, Traffic, Binding and Cellular Access of Vitamin D Sterols, *Bone and Mineral Res.*, Elsevier, 5:281-308 (1987).
Haddad, Vitamin D—Solar Rays, The Milky Way, or Both? *NEJM*, 326:1213-1215 (1992).
Haldimann et al., Effect of an Oral Dose of 25-Hydroxyvitamin D3 on Its Blood Levels in Patients with the Nephrotic Syndrome, *J Clin Endocrinology and Metabolism*, 50(3): 470-474 (1980).
Halloran et al., Plasma Vitamin D Metabolite Concentrations in Chronic Renal Failure: Effect of Oral Administration of 25-Hydroxyvitamin D3, *J. Clin. Endocrin. & Metab.*, 59:1063-1069 (1984).
Hamida et al., Hyperparathyroïdie secondaire álinsuffisance rénale *Annales d'Endocrinologie* 55:147-158 (1994) [reference in French]—abstract only.
Hannula et al., Constant, But Not Pulsed Calcitriol Suppresses Hemodialysis Patients' Antigen-Induced Lymphocyte Proliferation, *Nephron*, 86:139-144 (2000).
Hari et al., Vitamin D insufficiency and effect of cholecalciferol in children with chronic kidney disease, *Pediatr.Nephrol*,. 25: 2483-2488 (2010).
Hay et al., Vitamin D2 in Vertebrate Evolution, *Comp. Biochem. Physiol. B*, 56:375-380 (1977).
Hodson et al., Treatment of childhood renal osteodystrophy with calcitriol or ergocalciferol, *Clin Nephrology*, 24(4): 192-200 (1985).
Holick, Vitamin D Deficiency in CKD: Why Should We Care? *Am. J. Kidney Dis.*, 45:1119-1121 (2005).
Holick, Vitamin D Status: Measurement, Interpretation and Clinical Application, *Ann Epidemiol*, 19(2):73-78 (2009).
Holick, Vitamin D for health and in chronic kidney disease, Semin. Dial., 18(4):266-75 (2005).
Hollis, Circulating 25-Hydroxyvitamin D Levels Indicative of Vitamin D Sufficiency: Implications for Establishing a New Effective Dietary Intake Recommendation for Vitamin D, *J. Nutr.* 135: 317-322 (2005).
Horst et al., A Sensitive Competitive Protein Binding Assay for Vitamin D in Plasma, *Steroids*, 37:581-592 (1981).
Horst et al., Discrimination in the Metabolism of Orally Dosed Ergocalciferol and Cholecalciferol by the Pig, Rat and Chick, *Biochem. J.*, 204:185-189 (1982).
Horst et al., Rat cytochrome P450C24 (CYP24) does not metabolize 1,25-dihydroxyvitamin D2 to calcitroic acid, *J. Cell Biochem.*, 88:282-285 (2003).
Hottelart et al., Ostéodystrophie rénale (2): son traitement chez l'insuffisant rénal avant la dialyse *Nephrologie* 21(6):275-282 (2000) [reference in French]—abstract only.
Houghton et al., The Case Against Ergocalciferol (Vitamin D2) as a Vitamin Supplement, *Am. J. Clin. Nutr.*, 84:694-697 (2006).
Hunt et al., A Comparison of the Toxicity of Ergocalciferol and Cholecalciferol in Rhesus Monkeys (Macaca mulatta), J. Nutrition, 102:975-986 (1972).
Hussar, New Drugs of 1999, *J. Am. Pharmacist. Assoc.* 40(2):181-229 (2000).
International Search Report and Written Opinion for International Application No. PCT/US08/61594 (dated Jul. 28, 2008).
International Search Report for Application No. PCT/US2007/061521, dated Jul. 17, 2007.
International Search Report of counterpart PCT/US2008/061579 dated Aug. 21, 2008 (5 pages).
Ishimura et al., Serum Levels of 1,25-Dihydroxyvitamin D, 24,25-Dihydroxyvitamin D, and 25-Hydroxyvitamin D in Nondialyzed Patients with Chronic Renal Failure, *Kidney Int.*, 55:1019-1027 (1999).
Jara et al., Effect of Calcitriol Treatment and Withdrawal on Hyperparathyroidism in Haemodialysis Patients with Hypocalcaemia, *Nephrol. Dial. Transplant.*, 16:1009-1016 (2001).
Jean et al., Daily oral 25-hydroxycholecalciferol supplementation for vitamin D deficiency in haemodialysis patients: effects on mineral metabolism and bone markers Nephrol. Dial. Transplant 23(11):3670-3676 (2008).
Jean et al., Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment *Nephron. Clin. Pract.* 110:c58-c65 (2008).
Jean et al., Monthly cholecalciferol administration in heamodialysis patients: a simple and efficient strategy for vitamin D supplementation *Nephrol. Dial. Transplant* 24(12):3799-3805 (2009).
Jones, Pharmacokinetics of vitamin D toxicity, *Am. J. Clin. Nutr.* 88(suppl): 582S-6S (2008).
Jones., Expanding the Role for Vitamin D in Chronic Kidney Disease: Importance of Blood 25-OH-D Levels and Extra-Renal 1α-Hydroxyase in the Classical and Nonclassical Actions of 1α, 25-Dihydroxyvitamin D3, *Seminars in Dialysis*, 20(4):316-324 (2007).
Kajihara et al., Novel Method to Control Release of Lipophilic Drugs with High Potency from Silicone, *Chem. Pharm. Bull.*, 51:11-14 (2003).
Kalantar-Zadeh et al., Clinical Outcomes with Active versus Nutritional Vitamin D Compounds in Chronic Kidney Disease *Clin J Am Soc Nephrol.* 4(9):1529-1539 (2009).
Kanis et al., Rate of Reversal of Hypercalcaemia and Hypercalciuria Induced by Vitamin D and Its 1-alpha-Hydroxylated Derivatives, *BMJ*, 1:78-81 (1977).
Khachane et al., Novel Suatained Release Drug Delivery System: Review, *IJPRD*, 3(12):1-14 (2012).
Kim, *Advanced Pharmaceutics: Physicochemical Principles*, pp. 362-392, Boca Raton, Fla: CRC Press (2004).
Kinoshita et al., 1,25-Dihydroxyvitamin D Suppresses Circulating Levels of Parathyroid Hormone in a Patient with Primary Hyperparathyroidism and Coexistent Sarcoidosis, *J. Clin. Endo. & Metabol.*, 90(12):6727-6731 (2005).
Kleinman et al., Effects of Calcifediol on Calcified Tissue in Uremia, *Arch Intern Med*, 138: 864-865 (1978).
Kobayashi et al., 2β-(3-Hydroxyproxy)-α,25-Dihydroxyvitamin $D_3$ (ED-71), Preventive and Therapeutic Effects on Bone Mineral Loss in Ovariectomized Rats, *Bioorganic & Medicinal Chemistry Letters*, 3(9):1815-1819 (1993).

(56) References Cited

OTHER PUBLICATIONS

Kooienga et al., The effect of combined calcium and vitamin D3 supplementation on serum intact parathyroid hormone in moderate CKD, *Am.J.Kidney Dis*,. 53: 408-416 (2009).
Koshikawa et al., Clinical Effect of Intravenous Calcitriol Administration on Secondary Hyperparathyroidism, Nephron, 90:413-423 (2002).
LaClair et al., Prevalence of Calcidiol Deficiency in CKD: a Cross-Sectional Study Across Latitudes in the United States, *Am. J. Kidney Dis.*, 45:1026-1033 (2005).
Lafage et al., Ketodiet, Physiological Calcium Intake and Native Vitamin D Improve Renal Osteodystrophy, *Kidney Int.*, 42:1217-1225 (1992).
Lambert et al., Evidence for Extranrenal Production of 1-alpha,25-Dihydroxyvitamin D in Man, *J. Clin. Invest.*, 69:722-725 (1982).
Lambrey et al., 24, 25 Dihydroxycalciferol: Assay in Non-Anephric Patients on Chronic Haemodialysis and Assessment of it's Possible Pathophysiological Role in Renal Osteodystrophy *Proc Eur Dial Transplant Assoc.* 17:548-556 (1980).
Lambrey, Possible Link Between Changes in Plasma 24,25-Dihydroxyvitamin D and Healing of Bone Resorption in Dialysis Osteodrstrophy *Metab. Bone Dis. & Rel. Res.* 4:25-30 (1982).
Langman et al., 25-Hydroxyvitamin D3 (Calcifediol) Therapy of Juvenile Renal Osteodystrophy: Beneficial Effect on Linear Growth Velocity, *J. Pediatrics*, 100:815-820 (1982).
Larrosa et al., Long-Term Treatment of Hypovitaminosis D. Calcidol or Cholecalciferol? *Annals of the Rheumatic Diseases*, vol. 64, No. Suppl. 3, Jul. 2005, p. 366.
Lau et al., Vitamin D Therapy of Osteoporosis: Plain Vitamin D Therapy Versus Active Vitamin D Analog (D-Hormone) Therapy, *Calcif. Tissue Int.*, 65:295-306 (1999).
Lehmann et al., Coating of Tablets and Small Particles with Acrylic Resins by Fluid Bed Technology, *Int. J. Pharm. Tech. & Prod. Mfr.*, 2:31-43 (1981).
Letteri et al., Effects of 25-Hydroxycholecalciferol on Calcium Metabolism in Chronic Renal Failure Adv. Exp. Med. Biol. 81:591-601 (1977).
Lips et al., A global study of vitamin D status and parathyroid function in postmenopausal women with osteoporosis: baseline data from the multiple outcomes of raloxifene evaluation clinical trial, J. Clin. Endocrinol. Metab., 86(3):1212-21 (2001).
Lomonte et al., Are Low Plasma Levels of 25-(OH) Vitamin D a Major Risk Factor for Hyperparathyroidism Independent of Calcitriol in Renal Transplant Patients? *J. Nephrol.*, 18:96-101 (2005).
Lund et al., Serum 1,25-Dihydroxycholecalciferol in Anephric. Haemodialyzed and Kidney-transplanted Patients, *Nephron*, 25:30-33 (1980).
Maierhofer et al., Synthesis and Metabolic Clearance of 1,25-Dihydroxyvitamin D as Determinants of Serum Concentrations: a Comparison of Two Methods Journal of Clinical Endocrinology and Metabolism 53:472-475 (1981).
Manni et al., Oral Calcitriol: Comparison Between the Same Weekly Dose Administered as a Single vs. Two Divided Pulsed Doses in Secondary Hyperparathyroidism of Chronic Renal Failure, *Ital. J Mineral Electrolyte Metab.*, 11:61-64 (1997).
Martin et al., 19-Nor-1-α-25-Dihydroxyvitamin $D_2$ (Paricalcitol) Safely and Effectively Reduces the Levels of Intact Parathyroid Hormone in Patients on Hemodialysis, *J. Am. Soc. Nephrol.*, 9:1427-1432 (1998).
Matsushita et al., Clinical effects of 25-hydroxycholecalciferol in patients with chronic renal failure, *J Nutr Sci Vitaminol*, 23:257-261 (1977).
Mazouz et al., Risk factors of renal failure progression two years prior to dialysisis Clinical Nephroloby 51(6):355-366 (1999).
Mazur, Effects of 25-OHD3 on Renal Function in Pediatric Patients with Chronic Renal Failure, *Mineral Electrolyte Metab.* 10:351-358 (1984).
Memmos et al., Response of uremic osteoid to vitamin D, *Kidney Int*, 21(Suppl. 11): S50-S54 (1982).

Menon et al., Vitamin D insufficiency and hyperparathyroidism in children with chronic kidney disease, Pedaitr Nephrol, 23:1831-1836 (2008).
Messa et al., Direct In Vivo Assessment of Parathyroid Hormone-Calcium Relationship Curve in Renal Patients, *Kidney Int.*, 46:1713-1720 (1994).
Minutes of US FDA E&M Advisory Committee Meeting of Oct. 4, 1979 for Calderol® calcifediol capsules.
Moe et al., A randomized trial of cholecalciferol versus doxercalciferol for lowering parathyroid hormone in chronic kidney disease, *Clin. J.Am.Soc.Nephrol.* 5: 299-306 (2010).
Moe et al., Safety and Efficacy of Pulse and Daily Calcitriol in Patients on CAPD: a Randomized Trial, *Nephrol. Dial. Transplant.*, 13:1234-1241 (1998).
Morris, Cats Discriminate Between Cholecalciferol and Ergocalciferol, *J. Anim. Physiol, a. Anim. Nutr.*, 86:229-238 (2002).
Morris, Vitamin D: a Hormone for All Seasons—How Much is Enough? *Clin. Biochem. Rev.*, 26:21-32 (2005).
Muindi et al., Phamacokinetics of Liquid Calcitriol Formulation in Advanced Solid Tumor Patients: Comparison with Caplet Formulation, *Cancer Chemother. Pharmacol.*, 56:492-496 (2005).
Naik et al., Effects of Vitamin D Metabolites and Analogues on Renal Function, *Nephron*, 28:17-25 (1981).
Nakanishi et al., The Roles of Vitamin D in Secondary Hyperparathyroidism, [journal in Japanese] 52:1107-1112 (2004).
Norman et al. (eds.), *Vitamin D—Gene Regulation, Structure-Function Analysis and Clinical Application: Proceedings of the Eighth Workshop on Vitamin d Paris, France*, pp. 765-766, New York: Walter De Gruyter Inc. (1991).
Oksa et al., Effects of long-term cholecalciferol supplementation on mineral metabolism and calciotropic hormones in chronic kidney disease, *Kidney Blood Press Res.*, 31: 322-329 (2008).
Parfitt et al., Calcitriol But No Other Metabolite of Vitamin D is Essential for NormalBone Growth and Development in the Rat, *J. Clin. Invest.*, 73:576-586 (1984).
Patel et al., Glomerular Filtration Rate is a Major Determinant of the Relationship Between 25-Hydroxyvitamin D and Parathyroid Hormone, *Calcif. Tissue Int.*, 80:221-226 (2007).
Peacock et al., Effect of Calcium or 25OH Vitamin D3 Dietary Supplementation on Bone Loss at the Hip in Men and Women over the Age of 60 *The Journal of Clinical Endocrinology & Metabolism*, 85(9):3011-3019 (2007).
Perrie, Pharmaceutics: Drug Delivery and Targeting, Second Edition, Chapter 1 (2012).
Phadnis et al., Direct, Rapid Effects of 25-Hydroxyvitamin D3 on Isolated Intestinal Cells, *J. Cell. Biochem.*, 90:287-293 (2003).
Pourgholami et al., 1,25-Dihydroxyvitamin D3 Dissolved in Lipiodol Produces a Sustained Antiproliferative Effect in the Human Hepatoblastoma Cell Line HepG2, *Anticancer Res.*, 20:723-728 (2000).
Pourgholami et al., In Vitro Antiproliferative Activity of a Medium-Chain Triglyceride Solution of 1,25-Dihydroxyvitamin $D_3$ in HepG2 Cells, *Anticancer Res.*, 20:4257-4260 (2000).
Prescribing Information for Calderol® calcifediol capsules (1988).
Prescribing Information for Hectorol® (doxercalciferol capsules), Genzyme (2011).
Prescribing information for Zemplar® (paricalcitol) Capsules, Abbott (2011).
Prosecution History for U.S. Appl. No. 11/549,001, filed Oct. 12, 2006.
Prosecution History for U.S. Appl. No. 13/244,945, filed Sep. 26, 2011.
Rambeck et al., Biological Activity of 1α,25-Dihydroxyergocalciferol in Rachitic Chicks and in Rats, IZVIAK, 54(⅔):135-139 (1984).
Rapuri et al., Effect of Vitamins D2 and D3 Supplement Use on Serum 25-OHD Concentration in Elderly Women in Summer and Winter, Calcified Tissue International, 74(2):150-156 (2004).
Recker et al., The Efficacy of Calcifediol in Renal Osteodystrophy, *Arch. Intern. Med.*, 138:857-863 (1978).
Reddy et al., *Abstracts Sixth Annual Scientific Meeting of the American Society for Bone and Mineral Research*, 36:524 (1984).

(56) References Cited

OTHER PUBLICATIONS

Reichel et al., Calcium Metabolism in Early Chronic Renal Failure: Implications for the Pathogenesis of Hyperparathyroidism, *Nephrol. Dial. Transplant.*, 6:162-169 (1991).
Reichel et al., Intermittent Versus Continuous Administration of 1,25-dihydroxyvitamin D3 in experimental renal hyperparathyroidism, *Kidney Int.*, 44:1259-1265 (1993).
Reichel, Current treatment options in secondary renal hyperparathyroidism, *Nephrol Dial Transplant* 21:23-28 (2006).
Ritter et al., 25-Hydroxyvitamin D3 suppresses PTH synthesis and secretion by bovine parathyroid cells, *Kidney Int.*, 70:654-659 (2006).
Rix et al., Effect of 18 Months of Treatment with Alfacalcidol on Bone in Patients with Mild to Moderate Chronic Renal Failure, *Nephrol Dial Transplant*, 19:870-876 (2004).
Rucker et al., Vitamin D insufficiency and treatment with oral vitamin D3 in northern-dwelling patients with chronic kidney disease, *J.Nephrol.* 22: 75-82 (2009).
Russell et al., Therapeutic Effects of 25-Hydroxyvitamin D3 on Renal Osteodystrophy, *Mineral Electrolyte Metab.*, 1:129-138 (1978).
Rutherford et al., Effect of 25-Hydroxycholecalciferol on Calcium Absorption in Chronic Renal Disease, Kidney International, 8:320-324 (1975).
Saab et al., Prevalence of Vitamin D Deficiency and the Safety and Effectiveness of Monthly Ergocalciferol in Hemodialysis Patients, *Nephron Clin. Pract.*, 105:c132-c138 (2007).
Sanchez, Prevention and Treatment of Renal Osteodystrophy in Children With Chronic Renal Insufficiency and End-Stage Renal Disease, *Seminars in Nephrology*, 21:441-450 (2001).
Schmidt, Measurement of 25-Hydroxyvitamin D Revisited, *Clinical Chemistry*, 52(12):2304-2305 (2006).
Sebert et al. Comparative effects of equal doses of vitamin D2 and vitamin D3 for the correction of vitamin D deficiency in the elderly in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Sebert et al., Effets a Long Terme D'Une Association De 25-Hydroxycholécalciférol et de 1-Alpha-Hydroxycholécalciférol Sur L'Ostéodystrophie Des Hémodialysés Chroniques, *Rev. Rhum Mal Osteoartic* 48(7-9):535-541 (1981).
Sebert et al., Limit by Hyperphosphatemia of the Usefulness of Vitamin D Metabolites (1 alpha-Hydroxycholecalciferol and 25-Hydroxycholecalciferol) in the Treatment of Renal Osteodystrophy, *Metab. Bone Dis. & Rel. Res.*, 2:217-222 (1980).
Sekkarie, The Impact of Over-the-counter Vitamin D Suppiementals on Vitamin D and Parathyroid Hormone Levels in Chronic Kidney Disease, *Clin. Nephrology*, 65:91-96 (2006).
Shah et al., Prevalence and correction of 25(OH) vitamin D deficiency in peritoneal dialysis patients, *Peritoneal Dialysis Int.*, 25:362-366 ( 2005).
Shi et al., Preparation of Chitosan/Ethylcellulose Complex Microcapsule and its Application in Controlled Release of Vitamin $D_2$, *Biomaterials*, 23:4469-4473 (2002).
Sicinski et al., Synthesis of 1α,25-Dihydroxyvitamin D2, Its 24 Epimer and Related Isomers, and Their Binding Affinity for the 1,25-Dihydroxyvitamin D3 Receptor, Bioorganic Chemistry, 13: 158-169 (1985).
Singh et al., C-3 Epimers Can Account for a Significant Proportion of Total Circulating 25-Hydroxyvitamin D in Infants, Complicating Accurate Measurement and interpretation of Vitamin D Status, *J. Clin. Endo. & Metabol.*, 91(8):3055-3061 (2006).
Sjoden, et al., 1α-Hydroxyvitamin D2 is Less Toxic than 1α-Hydroxyvitamin D3 in the Rat, Society for Experimental Biology and Medicine, 179: 432-436 (1985).
Skelly et al., In vitro and in vivo testing an correlation for oral controlled/modified-release dosage forms. *Pharm. Res.*, 7(9):975-82 (1990).

Slatopolsky et al., Differential Effects of 19-nor-1,25-$(OH)_2D_2$ and 1α-Hydroxyvitamin $D_2$ on Calcium and Phosphorus in Normal and Uremic Rats, *Kidney International*, 62:1277-1284 (2002).
Somerville et al., Resistance to Parathyroid Hormone in Renal Failure: Role of Vitamin D Metabolites, *Kidney Int.*, 14:245-254 (1978).
Sommerfeldt et al., Metabolism of Orally Administered [3H]Ergocalciferol and [3H]Cholecalciferol by Dairy Calves, *J. Nutr.*, 113:2595-2600 (1983).
Sosa et al., The Effect of 25-dihydroxyvitamin D on the Bone Mineral Metabolism of Elderly Women with Hip Fracture, *Rheumatology*, 39:1263-1268 (2000).
Stamp et al., Comparison of Oral 25-Hydroxycholecalciferol, Vitamin D, and Ultraviolet Light as Determinants of Circulating 25-Hydroxyvitamin D, *The Lancet*, 1341-1343 (Jun. 25, 1977).
Stamp, Intestinal Absorption of 25-hydroxycholecalciferol, *The Lancet*, 121-123 (1974).
Stein et al., An Update on the Therapeutic Potential of Vitamin D Analogues, *Expert Opin. Investig. Drugs*, 12:825-840 (2003).
Stubbs et al., Cholecalciferol supplementation alters calcitriol-responsive monocyte proteins and decreases inflammatory cytokines in ESRD, *J.Am.Soc.Nephrol.*, 21: 353-361 (2010).
Stumpf, The Dose Makes the Medicine, *Drug Discovery Today*, 11:550-555 (2006).
Szycher, *Szycher's Dictionary of Biomaterials and Medical Devices*, pp. 20, 48, 127, Lancaster, Penn: Technomic Publishing Co., Inc. (1992).
Sömjen et al., Nonhypercalcemic Analogs of Vitamin D Stimulate Creatine Kinase B Activity in Osteoblast-Like ROS 17/2.8 Cells and Up-Regulate Their Responsiveness to Estrogens, *Steroids*, 63:340-343 (1998).
Taylor et al., Interrelationship of Serum 25-Hydroxyvitamin D3 and 1,25-Dihydroxyvitamin D in Juvenile Renal Osteodystrophy after Therapy with 25-Hydroxyvitamin D3, *Metab. Bone Dis. & Rel. Res.*, 4:255-261 (1982).
Taylor et al., The absence of 24,25-dihydroxycholecalciferol in anephric patients, *Clin.Sci.Mol.Med.Suppl.*, 55: 541-547 (1978).
Taylor, 24,25-Dihydroxyvitamin D in Human Serum. In: Vitamin D. Basic Research and Clinical Applications, pp. 197-203. Walter de Gruyter, New York (1979).
Teitelbaum et al., Calcifediol in Chronic Renal Insufficiency *JAMA* 235(2):164-167 (1976).
Teitelbaum et al., Tetracycline fluorescence in uremic and primary hyperparathyroid bone, *Kidney Int.*, 12:366-372 (1977).
Thomas et al., Hypovitaminosis D in Medical Inpatients, *NEJM*, 338:777-783 (1998).
Thombre, Assessment of the feasibility of oral controlled release in an exploratory development setting, *Drug Discovery Today*, 10(17): 1159-1166 (2005).
Tokmak et al., High-dose cholecalciferol to correct vitamin D deficiency in haemodialysis patients, *Nephrol.Dial.Transplant.*, 23: 4016-4020 (2008).
Trakarnvanich et al., Effect of high dose ergocalciferol in chronic kidney disease patients with 25-hydroxyvitamin D deficiency, *J.Med. Assoc.Thai.* 93: 885-891 (2010).
Tsuji, et al. A New and Convenient Synthesis of 1α,25-Dihydroxyvitamin D2 and It 24R-Epimer, Bull. Chem. Soc. Jpn., 62:10 pp. 3132-3137 (1989).
Tuohimaa et al., Both high and low levels of blood vitamin D are associated with a higher prostate cancer risk: a longitudinal, nested case-control study in the Nordic countries, Int. J. Cancer, 108(1):104-8 (2004).
US FDA Clinical Review and Evaluation of NDA for Calderol® calcifediol capsules (believed to be available circa 1983).
US FDA Summary of Basis of Approval for Calderol® calcifediol capsules (believed to be available circa 1980).
Van Weelden et al., Apoptotic Regression of MCF-7 Xenografts in Nude Mice Treated with the Vitamin $D_3$ Analog, EB1089, *Endocrinology*, 139:2102-2110 (1998).
Verberckmoes et al., Osteodystrophy of Dialysed Patients Treated with Vitamin D, *Proc Eur Dial Transplant Assoc.*, 10(0): 217-226 (1973).

(56) References Cited

OTHER PUBLICATIONS

Vieth, Vitamin D Supplementation, 25-Hydroxyvitamin D Concentrations, and Safety, Am. J. Clin. Nutr., 69:842-856 (1999).

Vieth, What is the optimal vitamin D status for health? *Prog. Biophys. Mol. Biol.*, 92:26-32 (2006).

Wise (ed.), *Handbook of Pharmaceutical Controlled Release Technology*, an Overview of Controlled Release Systems, Chapter 22, pp. 431-445, 461-463; Research and Development Aspects of Oral Controlled-Release Dosage Forms, Chapter 23, pp. 465-473, New York: Marcel Dekker, Inc. 3 (2000).

Witmer et al., Effects of 25-hydroxycholecalciferol on bone lesions of children with terminal renal failure *Kidney International* 10:395-408 (1976).

Wootton, Improving the Measurement of 25-Hydroxyvitamin D, *Clin Biochem Rev*, 26:33-36 (2005).

Written Opinion for Application No. PCT/US2007/061521, dated Jul. 17, 2007.

Written Opinion for Application No. PCT/US2008/061579, dated Aug. 21, 2008.

Yanoff et al., The Prevalence of Hypovitaminosis D and Secondary Hyperparathyroidism in Obese Black Americans, *Clin. Endocrinol. (Oxf)*, 64(5):523-529 (2006).

Zerwekh et al., Extra-Renal Production of 24,25-Dihydroxyvitamin D in Chronic Renal Failure During 25 Hydroxyvitamin D3 Therapy, *Kidney Int.*, 23:401-406 (1983).

Zisman et al., Impact of Ergocalciferol Treatment of Vitamin D Deficiency on Serum Parathyroid Hormone Concentrations in Chronic Kidney Disease, *Am. J. Nephrol.*, 27:36-43 (2007).

Zucchelli et al., Therapeutic effects of 25-hydroxycholecalciferol and sodium etidronate on renal osteodystrophy, *Mineral.Electrolyte Metab.* 7: 86-96 (1982).

\* cited by examiner

METHOD OF SAFELY AND EFFECTIVELY TREATING AND PREVENTING SECONDARY HYPERPARATHYROIDISM IN CHRONIC KIDNEY DISEASE

CROSS-REFERENCE TO RELATED APPLICATION

This is a continuation of U.S. patent application Ser. No. 14/291,666, filed May 30, 2014, which is a continuation of U.S. patent application Ser. No. 12/597,234, filed Dec. 4, 2009, which is the National Phase of International Application No. PCT/US2008/61594, filed Apr. 25, 2008, which claims the benefit of priority under 35 U.S.C. § 119(e) of U.S. Provisional Patent Application No. 60/913,850 filed Apr. 25, 2007. The disclosure of each priority application is incorporated herein by reference.

BACKGROUND

Secondary hyperparathyroidism is a disorder which develops primarily because of Vitamin D deficiency. It is characterized by abnormally elevated blood levels of parathyroid hormone (PTH) and, in the absence of early detection and treatment, it becomes associated with parathyroid gland hyperplasia and a constellation of metabolic bone diseases. It is a common complication of chronic kidney disease (CKD), with rising incidence as CKD progresses. Secondary hyperparathyroidism can also develop in individuals with healthy kidneys, due to environmental, cultural or dietary factors which prevent adequate Vitamin D supply.

"Vitamin D" is a term that refers broadly to the organic substances named Vitamin $D_2$, Vitamin $D_3$, Vitamin $D_4$, etc., and to their metabolites and hormonal forms that influence calcium and phosphorus homeostasis. "Vitamin D deficiency" is a term that broadly refers to reduced or low blood levels of Vitamin D, as defined immediately above.

The most widely recognized forms of Vitamin D are Vitamin $D_2$ (ergocalciferol) and Vitamin $D_3$ (cholecalciferol). Vitamin $D_2$ is produced in plants from ergosterol during sunlight exposure and is present, to a limited extent, in the human diet. Vitamin $D_3$ is generated from 7-dehydrocholesterol in human skin during exposure to sunlight and also is found, to a greater extent than Vitamin $D_2$, in the human diet, principally in dairy products (milk and butter), brain, certain fish and fish oils, and egg yolk. Vitamin D supplements for human use consist of either Vitamin $D_2$ or Vitamin $D_3$.

Both Vitamin $D_2$ and Vitamin $D_3$ are metabolized into prohormones by one or more enzymes located in the liver. The involved enzymes are mitochondrial and microsomal cytochrome P450 (CYP) isoforms, including CYP27A1, CYP2R1, CYP3A4, CYP2J3 and possibly others. These enzymes metabolize Vitamin $D_2$ into two prohormones known as 25-hydroxyvitamin $D_2$ and 24(S)-hydroxyvitamin $D_2$, and Vitamin $D_3$ into a prohormone known as 25-hydroxyvitamin $D_3$. The two 25-hydroxylated prohormones are more prominent in the blood, and are separately or collectively referred to as "25-hydroxyvitamin D". Vitamin $D_2$ and Vitamin $D_3$ can be metabolized into these same prohormones outside of the liver in certain epithelial cells, such as enterocytes, which contain the same (or similar) enzymes, but extrahepatic prohormone production probably contributes little to blood levels of 25-hydroxyvitamin D.

The rates of hepatic and extrahepatic production of the Vitamin D prohormones are not tightly regulated, and they vary mainly with intracellular concentrations of the precursors (Vitamin $D_2$ and Vitamin $D_3$). Higher concentrations of either precursor increase prohormone production, while lower concentrations decrease production. Hepatic production of prohormones is inhibited by high levels of 25-hydroxyvitamin D via a poorly understood mechanism apparently directed to prevention of excessive blood prohormone levels. However, there is little evidence of feedback regulation of extrahepatic prohormone production.

The Vitamin D prohormones are further metabolized in the kidneys into potent hormones by an enzyme known as CYP27B1 (or 25-hydroxyvitamin $D_3$-1α-hydroxylase) located in the proximal kidney tubule. The prohormones 25-hydroxyvitamin $D_2$ and 24(S)-hydroxyvitamin $D_2$ are metabolized into hormones known as 1α,25-dihydroxyvitamin $D_2$ and 1α,24(S)-dihydroxyvitamin $D_2$. Likewise, 25-hydroxyvitamin $D_3$ is metabolized into a hormone known as 1α,25-dihydroxyvitamin $D_3$ (or calcitriol). These hormones are secreted by the kidneys into the blood for systemic delivery. The two 25-hydroxylated hormones, usually far more prominent in the blood than 1α,24(S)-dihydroxyvitamin $D_2$, are separately or collectively referred to as "1,25-dihydroxyvitamin D". Vitamin D prohormones can be metabolized into hormones outside of the kidneys in keratinocytes, lung epithelial cells, enterocytes, cells of the immune system (e.g., macrophages) and certain other cells containing CYP27B1 or similar enzymes, but such extrarenal hormone production is incapable of sustaining normal blood levels of 1,25-dihydroxyvitamin D in advanced CKD. Extrarenal hormone production permits intracellular concentrations of 1,25-dihydroxyvitamin D to exceed and be independent of blood levels of 1,25-dihydroxyvitamin D.

Blood levels of 1,25-dihydroxyvitamin D are precisely regulated by a feedback mechanism which involves PTH. The renal 1α-hydroxylase (or CYP27B1) is stimulated by PTH and inhibited by 1,25-dihydroxyvitamin D. When blood levels of 1,25-dihydroxyvitamin D fall, the parathyroid glands sense this change via intracellular Vitamin D receptors (VDR) and secrete PTH. The secreted PTH stimulates expression of renal CYP27B1 and, thereby, increases production of Vitamin D hormones. As blood concentrations of 1,25-dihydroxyvitamin D rise again, the parathyroid glands attenuate further PTH secretion. As blood PTH levels fall, renal production of Vitamin D hormones decreases. Rising blood levels of 1,25-dihydroxyvitamin D also directly inhibit further Vitamin D hormone production by CYP27B1. PTH secretion can be abnormally suppressed in situations where blood 1,25-dihydroxyvitamin D concentrations become excessively elevated, as can occur in certain disorders or more commonly as a result of bolus (usually intravenous) doses of Vitamin D hormone replacement therapies. Oversuppression of PTH secretion can cause or exacerbate disturbances in calcium homeostasis and has been linked to vascular calcification. The parathyroid glands and the renal CYP27B1 are so sensitive to changes in blood concentrations of Vitamin D hormones that serum 1,25-dihydroxyvitamin D is tightly controlled, fluctuating up or down by less than 20% during any 24-hour period. In contrast to renal production of Vitamin D hormones, extrarenal production is not under precise feedback control.

The Vitamin D hormones have essential roles in human health which are mediated by the intracellular VDR. In particular, the Vitamin D hormones regulate blood calcium levels by controlling intestinal absorption of dietary calcium and reabsorption of calcium by the kidneys. The Vitamin D hormones also participate in the regulation of cellular differentiation and growth and normal bone formation and metabolism. Further, Vitamin D hormones are required for the normal functioning of the musculoskeletal, immune and renin-angiotensin systems. Numerous other roles for Vitamin D hormones are being postulated and elucidated, based on the documented presence of intracellular VDR in nearly every human tissue.

The actions of Vitamin D hormones on specific tissues depend on the degree to which they bind to (or occupy) the intracellular VDR in those tissues. The three Vitamin D hormones specifically discussed herein have nearly identical affinities for the VDR and, therefore, have essentially equivalent VDR binding when present at the same intracellular concentrations. VDR binding increases as the intracellular concentrations of the hormones rise, and decreases as the intracellular concentrations fall. Intracellular concentrations of the Vitamin D hormones change in direct proportion to changes in blood hormone concentrations with the exception that in cells containing CYP27B1 (or similar enzymes), intracellular concentrations of the Vitamin D hormones also change in direct proportion to changes in blood and/or intracellular prohormone concentrations, as discussed above. In such cells, adequate intracellular prohormone concentrations can prevent reductions in intracellular 1,25-dihydroxyvitamin D concentrations due to low blood levels of 1,25-diydroxyvitamin D.

Vitamin $D_2$, Vitamin $D_3$ and their prohormonal forms have affinities for the VDR which are estimated to be at least 100-fold lower than those of the Vitamin D hormones. As a consequence, physiological concentrations of these hormone precursors exert little, if any, biological actions without prior metabolism to Vitamin D hormones. However, supraphysiological levels of these hormone precursors, especially the prohormones, in the range of 10 to 1,000 fold higher than normal, can sufficiently occupy the VDR and exert actions like the Vitamin D hormones.

Blood levels of Vitamin $D_2$ and Vitamin $D_3$ are normally present at stable, concentrations in human blood, given a sustained, adequate supply of Vitamin D from sunlight exposure and an unsupplemented diet. Slight, if any, increases in blood Vitamin D levels occur after meals since unsupplemented diets have low Vitamin D content, even those containing foods fortified with Vitamin D. The Vitamin D content of the human diet is so low that the National Institutes of Health (NIH) cautions "it can be difficult to obtain enough Vitamin D from natural food sources" [NIH, Office of Dietary Supplements, Dietary Supplement Fact Sheet: Vitamin D (2005)]. Almost all human Vitamin D supply comes from fortified foods, exposure to sunlight or from dietary supplements, with the last source becoming increasingly important. Blood Vitamin D levels rise only gradually, if at all, after sunlight exposure since cutaneous 7-dehydrocholesterol is modified by UV radiation to pre-Vitamin $D_3$ which undergoes thermal conversion in the skin to Vitamin $D_3$ over a period of several days before circulating in the blood.

Blood Vitamin D hormone concentrations also remain generally constant through the day in healthy individuals, but can vary significantly over longer periods of time in response to seasonal changes in sunlight exposure or sustained alterations in Vitamin D intake. Marked differences in normal Vitamin D hormone levels are commonly observed between healthy individuals, with some individuals having stable concentrations as low as approximately 20 pg/mL and others as high as approximately 70 pg/mL. Due to this wide normal range, medical professionals have difficulty interpreting isolated laboratory determinations of serum total 1,25-dihydroxyvitamin D; a value of 25 pg/mL may represent a normal value for one individual or a relative deficiency in another.

Transiently low blood levels of 1,25-dihydroxyvitamin D stimulate the parathyroid glands to secrete PTH for brief periods ending when normal blood Vitamin D hormone levels are restored. In contrast, chronically low blood levels of 1,25-dihydroxyvitamin D continuously stimulate the parathyroid glands to secrete PTH, resulting in a disorder known as secondary hyperparathyroidism. Chronically low hormone levels also decrease intestinal calcium absorption, leading to reduced blood calcium concentrations (hypocalcemia) which further stimulate PTH secretion. Continuously stimulated parathyroid glands become increasingly hyperplastic and eventually develop resistance to regulation by Vitamin D hormones. Without early detection and treatment, followed by consistent maintenance or preventative therapy, secondary hyperparathyroidism progressively increases in severity, causing debilitating metabolic bone diseases, including osteoporosis and renal osteodystrophy. Appropriate prophylactive therapy for early stage CKD can delay or prevent the development of secondary hyperparathyroidism.

Chronically low blood levels of 1,25-dihydroxyvitamin D develop when there is insufficient renal CYP27B1 to produce the required supply of Vitamin D hormones, a situation which commonly arises in CKD. The activity of renal CYP27B1 declines as the Glomerular Filtration Rate (GFR) falls below approximately 60 ml/min/1.73 $m^2$ due to the loss of functioning nephrons. In end-stage renal disease (ESRD), when the kidneys fail completely and hemodialysis is required for survival, renal CYP27B1 often becomes altogether absent. Any remaining CYP27B1 is greatly inhibited by elevated serum phosphorous (hyperphosphatemia) caused by inadequate renal excretion of dietary phosphorous.

Chronically low blood levels of 1,25-dihydroxyvitamin also develop because of a deficiency of Vitamin D prohormones, since renal hormone production cannot proceed without the required precursors. Prohormone production declines markedly when cholecalciferol and ergocalciferol are in short supply, a condition often described in the medical literature by terms such as "Vitamin D insufficiency", "Vitamin D deficiency" or "hypovitaminosis D". Therefore, measurement of prohormone (serum total 25-hydroxyvitamin D) levels in blood has become the accepted method among healthcare professionals to monitor Vitamin D status. Recent studies have documented that the great majority of CKD patients have low blood levels of 25-hydroxyvitamin D, and that the prevalence of Vitamin D insufficiency and deficiency increases as CKD progresses.

It follows that individuals most vulnerable to developing chronically low blood levels of 1,25-dihydroxyvitamin D are those with CKD. Most CKD patients typically have decreased levels of renal CYP27B1 and a shortage of 25-hydroxyvitamin D prohormones. Not surprisingly, most CKD patients develop secondary hyperparathyroidism. Unfortunately, early detection and treatment of secondary hyperparathyroidism in CKD is rare, let alone prevention.

The National Kidney Foundation (NKF) has recently focused the medical community's attention on the need for early detection and treatment of secondary hyperparathyroidism by publishing Kidney Disease Outcomes Quality Initiative (K/DOQI) Clinical Practice Guidelines for Bone Metabolism and Disease in Chronic Kidney Disease [*Am. J. Kidney Dis.* 42:S1-S202, 2003)]. The K/DOQI Guidelines identified the primary etiology of secondary hyperparathyroidism as chronically low blood levels of 1,25-dihydroxyvitamin and recommended regular screening in CKD Stages 3 through 5 for elevated blood PTH levels relative to stage-specific PTH target ranges, which for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1). In the event that screening revealed an iPTH value to be above the ranges targeted for CKD Stages 3 and 4, the Guidelines recommended a follow-up evaluation of serum total 25-hydroxyvitamin D to detect possible Vitamin D insufficiency or deficiency. If 25-hydroxyvitamin D below 30 ng/mL was observed, the recommended intervention was Vitamin D repletion therapy using orally administered ergocalciferol. If 25-hydroxyvitamin D above 30 ng/mL was observed, the recommended intervention was Vitamin D hormone replacement therapy using oral or intravenous Vitamin D hormones or analogs.

Current Vitamin D hormone replacement therapies available for use in CKD patients contain 1,25-dihydroxyvitamin $D_3$, 19-nor-1,25-dihdroxyvitamin $D_2$, or 1-alpha-hydroxyvitamin $D_2$ and are formulated for quick or immediate release in the gastrointestinal tract or for bolus intravenous administration. When administered at chronically high doses (usually 0.25 to 2.0 mcg orally, or 1.0 to 10 mcg intravenously), as is usually required for adequate hormone replacement, these products can effectively restore serum total 1,25-dihydroxyvitamin D to levels above 20 pg/mL and lower iPTH by at least 30% in the majority of patients. However, they cannot be administered in high enough doses to control elevated iPTH in all patients and they sporadically cause side effects, including hypercalcemia, hyperphosphatemia, hyercalciuria and oversuppression of iPTH, in a significant minority of the patients. Health care professionals are cautious in raising the dose of these hormone replacement therapies for purposes of improving the control of secondary hyperparathyroidism in patients with excessive iPTH levels due to the increasing risk of causing such side effects.

As explained above, all CKD patients eventually develop decreased levels of renal CYP27B1 as kidney insufficiency becomes more severe, making it even more difficult, and eventually impossible, to treat secondary hyperparathyroidism with Vitamin D repletion therapies alone. The safe and effective use of Vitamin D hormone replacement therapies, therefore, is essential in the later stages of CKD.

Clearly, a novel alternative approach to Vitamin D hormone replacement for the treatment and prevention of secondary hyperparathyroidism in CKD Stages 3-5 is sorely needed, in view of the problems encountered with the currently available oral and intravenous Vitamin D hormone therapies.

BRIEF DESCRIPTION OF THE INVENTION

In one aspect the present invention provides a method of treating and preventing secondary hyperparathyroidism in CKD by increasing or maintaining blood concentrations of both 25-hydroxyvitamin D and 1,25-dihydroxyvitamin D in a patient by administering 25-hydroxyvitamin $D_3$ with or without 25-hydroxyvitamin $D_2$ and, as necessary, 1,25-dihydroxyvitamin $D_2$ as a Vitamin D hormone replacement therapy. The blood concentrations of 25-hydroxyvitamin D are increased to and maintained at or above 30 ng/mL, with 25-hydroxyvitamin $D_3$ being the predominant hormone, and blood concentrations of serum total 1,25-dihydroxyvitamin $D_2$ are increased to or maintained within a patient's normal historical physiological range for serum total 1,25-dihydroxyvitamin D without causing side effects, including hypercalcemia, hyperphosphatemia, hypercalciuria and oversuppression of iPTH, in a significant minority of the patients.

In another aspect, the invention provides a method of concurrently lowering or maintaining plasma iPTH levels, increasing or maintaining serum calcium levels, maintaining serum phosphorous levels, increasing or maintaining serum 25-hydroxyvitamin D, or increasing or maintaining serum 1,25-dihydroxyvitamin D levels in a human patient by administering to the early stage CKD patient, 25-hydroxyvitamin $D_3$ with or without 25-hydroxyvitamin $D_2$ and, as necessary, 1,25-dihydroxyvitamin $D_2$, so that the blood concentrations of 25-hydroxyvitamin D are increased to and maintained at or above 30 ng/mL, with 25-hydoxyvitamin $D_3$ being the predominant hormone, and blood concentrations of 1,25-dihydroxyvitamin D are increased to or maintained within a patient's normal historical physiological range for 1,25-dihydroxyvitamin D.

In yet another aspect, the invention provides a method of reducing the risk of over suppression of plasma iPTH levels in a patient undergoing treatment for elevated levels of plasma iPTH, or maintenance/prevention therapy for secondary hyperparathyroidism by administering 25-hydroxyvitamin $D_3$ with or without 25-hydroxyvitamin $D_2$ and, as necessary, 1,25-dihydroxyvitamin $D_2$, so that the blood concentrations of 25-hydroxyvitamin D are increased to and maintained at or above 30 ng/mL, with 25-hydoxyvitamin $D_3$ being the predominant hormone, and blood concentrations of 1,25-dihydroxyvitamin D are increased to or maintained within a patient's normal historical physiological range for 1,25-dihydroxyvitamin D, and elevated plasma iPTH levels are decreased or controlled while avoiding an abnormally low bone turnover rate.

In another aspect, the invention provides a method of proactively administering 25-hydroxyvitamin $D_3$ with or without 25-hydroxyvitamin $D_2$, and/or Vitamin $D_3$ with or without Vitamin $D_2$, to an early stage CKD patient having the potential to develop secondary hyperparathyroidism due to Vitamin D insufficiency or deficiency.

Given this invention, which is described in more detail herein, it becomes possible, for the first time, to (1) effectively and safely use 25-hydroxyvitamin $D_3$ with or without 25-hydroxyvitamin $D_2$, and/or Vitamin $D_3$ with or without Vitamin $D_2$, to treat secondary hyperparathyroidism due to Vitamin D insufficiency or deficiency in the early stages of CKD; (2) concurrently apply these Vitamin D repletion therapies and Vitamin D hormone replacement therapies for more effective treatment of secondary hyperparathyroidism in this population; (3) prevent the recurrence of secondary hyperparathyroidism due to Vitamin D insufficiency of deficiency after initial diagnosis and treatment with Vitamin D repletion therapies; and (4) prevent the development of Vitamin D insufficiency and deficiency altogether by proactive administration of Vitamin D repletion therapy.

A fuller appreciation of the specific attributes of this invention will be gained upon an examination of the following detailed description of preferred embodiments, and the appended claim. Before the embodiments of the invention are explained in detail, it is to be understood that the invention is not limited in its application to the details of construction and the arrangements of the components set forth in the following description. The invention is capable of other embodiments and of being practiced or being carried out in various ways. Also, it is understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof.

DETAILED DESCRIPTION OF THE INVENTION

The present invention relates to treating and preventing secondary hyperparathyroidism and the underlying chronically low blood levels of 1,25-dihydroxyvitamin D by administering safe and effective amounts of Vitamin D repletion therapy with, as necessary, 1,25-dihydrovitamin $D_2$. It has been discovered that secondary hyperparathyroidism arising in CKD is frequently unresponsive to Vitamin D repletion therapy unless such therapy specifically elevates serum total 25-hydroxyvitamin D to levels of at least 30 ng/mL and consistently maintains such levels in a manner which ensures that the predominant circulating prohormone is 25-hydroxyvitamin $D_3$. Without ensuring the predominance of circulating 25-hydroxyvitamin $D_3$, adequate production of 1,25-dihydroxyvitamin D by the remaining renal CYP271B is not fully supported, making control of chronically elevated PTH (or secondary hyperparathyroidism) incomplete or unlikely. Current approaches to administering Vitamin D replacement therapies to CKD patients overwhelmingly favor or promote the elevation of serum total 25-hydroxyvitamin D in such a manner that 25-hydroxyvitamin $D_2$ becomes the predominant circulating prohormone, due to its perceived safety advantage.

It has been further found that elevated levels of circulating either 25-hydroxyvitamin $D_2$ or 25-hydroxyvitamin $D_4$, in the presence of 25-hydroxyvitamin $D_3$, do not strongly support the production of 1,25-dihydroxyvitamin $D_2$ or 1,25-dihydroxyvitamin $D_4$, respectively, and instead support the predominant production of other metabolites, including 24,25-dihydroxyvitamin $D_2$ and 24,25-dihydroxyvitamin $D_4$. Unlike 1,25-dihydroxyvitamin $D_2$ or 1,25-dihydroxyvitamin $D_4$, these alternative metabolites do not potently inhibit the secretion of PTH by the parathyroid glands in secondary hyperparathyroidism.

In one aspect the present invention consists of increasing and then maintaining blood concentrations of 25-hydroxyvitamin D at or above 30 ng/mL, and blood concentrations of 1,25-dihydroxyvitamin D to within a patient's normal historical physiological range for 1,25-dihydroxyvitamin D by administering 25-hydroxyvitamin $D_3$ with or without a lesser amount of 25-hydroxyvitamin $D_2$ and/or Vitamin $D_3$ with or without a lesser amount of Vitamin $D_2$. As noted hereinbefore, many circumstances can lead to chronically low blood levels of 1,25-dihydroxyvitamin D, including the development of CKD, living in northern latitudes and insufficient intake of cholecalciferol and/or ergocalciferol. It has been found that chronic treatment of those CKD patients in need thereof with appropriate, effective and progressively adjusted Vitamin D repletion therapy with, as necessary, 1,25-dihydroxyvitamin $D_2$, can provide blood concentrations of 25-hydroxyvitamin D consistently at or above 30 ng/mL, with 25-hydroxyvitamin $D_3$ being the predominant circulating hormone, and blood concentrations of 1,25-dihydroxyvitamin D consistently within the patient's normal historical physiological range, which together can reduce and often normalize elevated plasma PTH levels and subsequently maintain reduced or normalized plasma PTH levels.

In another aspect, the invention provides a method of concurrently lowering or maintaining plasma iPTH levels, increasing or maintaining serum calcium levels, maintaining serum phosphorous levels, increasing or maintaining serum 25-hydroxyvitamin D levels, and increasing or maintaining serum 1,25-dihydroxyvitamin D levels in a human patient by chronically administering to the patient appropriate, effective and progressively adjusted amounts of Vitamin D repletion therapy with, as necessary, one or more Vitamin D hormone replacement therapies. Many diseases manifest abnormal blood levels of one or more prohormones, hormones and minerals. In CKD, for example, patients may experience decreases in serum total 25-hydroxyvitamin D, and/or 1,25-dihydroxyvitamin D, increases in plasma iPTH, decreases in serum calcium and increases in serum phosphorous. Consistent therapeutic and, then, prophylactic treatment in accordance with the present invention presents concurrent leveling and/or maintaining of the prohormone, hormone and mineral levels.

In yet another aspect, the invention provides a method of proactively administering 25-hydroxyvitamin $D_3$ with or without a lesser amount of 25-hydroxyvitamin $D_2$, and/or Vitamin $D_3$ with or without a lesser amount of Vitamin $D_2$, to an early stage CKD patient having the potential to develop secondary hyperparathyroidism due to Vitamin D insufficiency or Vitamin D deficiency with the result that blood concentrations of 25-hydroxyvitamin D are maintained consistently at or above 30 ng/mL, with 25-hydroxyvitamin $D_3$ being the predominant circulating hormone, and blood concentrations of 1,25-dihydroxyvitamin D are maintained consistently within the patient's normal historical physiological range, and plasma PTH is maintained at reduced or normal levels.

Preferably blood concentrations of 25-hydroxyvitamin D are maintained consistently at or above 30 ng/mL, with 25-hydroxyvitamin $D_3$ being the predominant circulating hormone, for at least 14 days, at least 1 month, at least 30 days, at least 2 months, at least three months, at least 90 days, or at least 6 months. Further preferably, blood concentrations of 1,25-dihydroxyvitamin D are maintained consistently within the patient's normal historical physiological range, and plasma PTH is maintained at reduced or normal levels, for at least 14 days, at least 1 month, at least 30 days, at least 2 months, at least three months, at least 90 days, or at least 6 months.

"Vitamin D insufficiency and deficiency" is generally defined as having serum 25-hydroxyvitamin D levels below 30 ng/mL (equivalent to about 75 nmol/L) (National Kidney Foundation guidelines, NKF, Am. J. Kidney Dis. 42:S1-S202 (2003), incorporated herein by reference).

The term "vitamin $D_2$ compound" as used herein refers to a precursor, analog or derivative of ergocalciferol, 25-hydroxyvitamin $D_2$ or 1,25-dihydroxyvitamin $D_2$.

The term "vitamin $D_3$ compound" as used herein refers to a precursor, analog or derivative of vitamin $D_3$ (cholecalciferol), 25-hydroxyvitamin $D_3$, or 1α,25-dihydroxyvitamin $D_3$, including, 1α-hydroxyvitamin $D_3$, that activates the vitamin D receptor or that can be metabolically converted in a human to a compound that activates the vitamin D receptor.

As used herein, the term "patient's normal historical physiological range of serum 1,25-dihydroxyvitamin D" refers to the average blood concentration range of 1,25-dihydroxyvitamin D of a patient based on at least two annual or biannual readings of serum 1,25-dihydroxyvitamin D levels taken while the kidneys are healthy.

As used herein the term "hypercalcemia" refers to condition in a patient wherein the patient has corrected serum levels of calcium above 10.2 mg/dL. Normal corrected serum levels of calcium for a human are between about 8.6 to 10.2 mg/dL.

As used herein the term "hyperphosphatemia" refers to a condition in a patient having normal kidney function, or Stage 1-4 CKD, wherein the patient has serum phosphorous levels above 4.6 mg/dL. In a patient who has Stage 5 CKD, hyperphosphatemia occurs when the patient has serum levels above 5.5 mg/dL. Normal values for serum phosphorous in a human are 2.4-4.5 mg/dL.

As used herein the term "over suppression of plasma iPTH" refers to a condition in a patient having adequate kidney function, or Stage 1-3 CKD, wherein the patient has levels of plasma iPTH below 15 pg/mL. In a patient having Stage 4 CKD, over suppression of plasma iPTH occurs when the patient has levels of plasma iPTH below 30 pg/mL. In a patient having Stage 5 CKD, over suppression of plasma iPTH occurs when the patient has levels of plasma iPTH below 150 pg/mL.

As used herein, the term "Vitamin D repletion therapy" refers to the administration to a patient of an effective amount of a vitamin $D_3$ compound with a vitamin D compound, e.g., cholecalciferol with or without a lesser amount of ergocalciferol, and/or 25-hydroxyvitamin $D_3$ with or without a lesser amount of 25-hydroxyvitamin $D_2$ via any route of administration.

As used herein, the term "Vitamin D hormone replacement therapy" refers to the administration to a patient of an effective amount of 1,25-dihydroxyvitamin $D_2$, 1,25-dihydroxyvitamin $D_3$, 1,25-dihydroxyvitamin $D_4$, or other metabolites and analogs of Vitamin D which can substantially occupy the intracellular VDR.

The term "therapeutically effective amount" depends on the patient's condition and is an amount effective to achieve a desired clinical effect, e.g. to maintain a laboratory test value within the normal range or the recommended range for that patient's condition, or an amount effective to reduce the occurrence or severity of a clinical sign or symptom of disease. In some embodiments, a therapeutically effective amount is an amount effective on average to maintain serum 25-hydroxyvitamin D levels or 25-hydroxyvitamin $D_3$ levels at about 30 ng/mL (equivalent to about 75 nmol/L) or higher. Such levels may be maintained for an extended period, for example at least one month, at least three months, at least six months, nine months, one year, or longer. In other embodiments, a therapeutically effective amount is an amount effective on average to achieve at least a 15%, 20%, 25% or 30% reduction in serum parathyroid hormone levels (iPTH) from baseline levels without treatment. In yet other embodiments, a therapeutically effective amount is an amount effective on average to reach CKD stage-specific iPTH target ranges which for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1). When used in reference to an amount of a vitamin $D_3$ compound, "therapeutically effective" can refer either to the effective amount of vitamin $D_3$ supplement when administered alone, or to the effective amount of vitamin $D_3$ compound when administered in combination with a vitamin $D_2$ compound.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

Ergocalciferol, cholecalciferol, 25-hydroxyvitamin $D_2$ and/or 25-hydroxyvitamin $D_3$, 1,25-dihydroxyvitamin $D_2$, and analogs thereof are useful as pharmacologically active compounds of this invention. The pharmacologically active compounds of this invention can be processed in accordance with conventional methods of pharmacy to produce pharmaceutical agents for administration to patients, e.g., in admixtures with conventional excipients such as pharmaceutically acceptable organic or inorganic carrier substances suitable for parenteral, enteral (e.g., oral), topical or transdermal application which do not deleteriously react with the active compounds. Suitable pharmaceutically acceptable carriers include, but are not limited to, water, salt (buffer) solutions, alcohols, gum arabic, mineral and vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic active compounds. If a pharmaceutically acceptable solid carrier is used, the dosage form of the analogs may be tablets, capsules, powders, suppositories, or lozenges. If a liquid carrier is used, soft gelatin capsules, transdermal patches, aerosol sprays, topical creams, syrups or liquid suspensions, emulsions or solutions may be the dosage form.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragées, liquids, drops, suppositories, or capsules such as soft gelatin capsules. A syrup, elixir, or the like can be used wherein a sweetened vehicle is employed.

Sustained or directed release compositions can be formulated, e.g., liposomes or those wherein the active compound is protected with differentially degradable coatings, such as by microencapsulation, multiple coatings, etc. It is also possible to freeze-dry the new compounds and use the lypolizates obtained, for example, for the preparation of products for injection. Transdermal delivery of pharmaceutical compositions of the compounds of the invention is also possible.

For topical application, there are employed as nonsprayable forms, viscous to semi-solid or solid forms comprising a carrier compatible with topical application and having a dynamic viscosity preferably greater than water. Suitable formulations include, but are not limited to, solutions, suspensions, emulsions, creams, ointments, powders, liniments, salves, aerosols, etc., which are, if desired, sterilized or mixed with auxiliary agents, e.g., preservatives, etc.

It is possible, if desired, to produce the metabolites of certain ones of the compounds of the invention, in particular by nonchemical means. For this purpose, it is possible to convert them into a suitable form for administration together with at least one vehicle or auxiliary and, where appropriate, combined with one or more other active compounds.

The dosage forms may also contain adjuvants, such as preserving or stabilizing adjuvants. They may also contain other therapeutically valuable substances or may contain more than one of the compounds specified herein and in the claims in admixture.

As described hereinbefore, Vitamin D repletion and Vitamin D hormone replacement therapies are preferably administered to the human patients in oral or intravenous dosage formulations. The administration of such therapies, in accordance with the present invention, can be on an episodic basis, suitably from daily, to 1 to 3 times a week. Suitably the dosage of Vitamin D replacement therapy or Vitamin D hormone replacement therapy is about 0.5 µg to about 400 µg per week, depending on the agent selected. Suitably such therapies can be given in a unit dosage form between about 0.5 µg to about 100 µg, or about 0.5 µg to about 10 µg in a pharmaceutically acceptable carrier per unit dosage. Episodic doses can be a single dose or, optionally, divided into 2-4 subdoses which, if desired, can be given, e.g., twenty minutes to an hour apart until the total dose is given.

Those of ordinary skill in the art will readily optimize effective doses and co-administration regimens as determined by good medical practice and the clinical condition of the individual patient. Regardless of the manner of administration, it will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, sex, body weight, general state of health, on diet, on the timing and mode of administration, on the rate of excretion, and on medicaments used in combination and the severity of the particular disorder to which the therapy is applied. Dosages for a given patient can be determined using conventional considerations, e.g., by customary comparison of the differential activities of the subject compounds and of a known agent, such as by means of an appropriate conventional pharmacological protocol. A physician of ordinary skill can readily determine and prescribe the effective amount of the drug required to counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. The dosage of active ingredient in the compositions of this invention may be varied; however, it is necessary that the amount of the active ingredient be such that an efficacious dosage is obtained. The active ingredient is administered to patients (animal and human) in need of treatment in dosages that will provide optimal pharmaceutical efficacy.

Bulk quantities of Vitamin D and Vitamin D analogs in accordance with the present invention can be readily obtained in accordance with the many widely known processes.

The compositions, methods and kits of the invention are useful for treating any subject in need of vitamin D supplementation, either prophylactically to prevent vitamin D insufficiency or deficiency, or therapeutically to replete low serum vitamin 25(OH)D levels to normal range or above. The compositions and methods of the invention are also useful for preventing or treating secondary hyperparathyroidism resulting from low vitamin D levels. In general, serum 25(OH)D values less than 5 ng/mL indicate severe deficiency associated with rickets and osteomalacia. Although 30 ng/mL has been suggested as the low end of the normal range, more recent research suggests that PTH levels and calcium absorption are not optimized until serum total 25(OH)D levels reach approximately 40 ng/mL. [See also Vieth, R. Prog Biophys Mol Biol. 2006 September; 92(1): 26-32.] The term "subject" or "patient" as used herein includes humans, mammals (e.g., dogs, cats, rodents, sheep, horses, cows, goats), veterinary animals and zoo animals.

Patients in need of vitamin D supplementation include healthy subjects and subjects at risk for vitamin D insufficiency or deficiency, for example, subjects with stage 1, 2, 3, 4 or 5 chronic kidney disease; infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D in skin during exposure to sunlight and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with an Sun Protection Factor (SPF) of 8 reduces production of vitamin D by 95%, and higher SPFs may further reduce cutaneous vitamin D production); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenytoin, fosphenytoin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); subjects with osteoporosis and/or postmenopausal women. According to the Institute of Medicine's report on the Dietary Reference Intakes for vitamin D, food consumption data suggest that median intakes of vitamin D for both younger and older women are below current recommendations; data suggest that more than 50% of younger and older women are not consuming recommended amounts of vitamin D. Optionally excluded from the methods of the invention are therapeutic treatment of subjects suffering from renal osteodystrophy (including osteomalacia and osteitis fibrosa cystica).

In other aspects, the compositions and methods of the invention are useful for prophylactic or therapeutic treatment of vitamin D-responsive diseases, i.e., diseases where vitamin D, 25(OH)D or active vitamin D (e.g., 1, 25(OH)$_2$D) prevents onset or progression of disease, or reduces signs or symptoms of disease. Such vitamin D-responsive diseases include cancer (e.g., breast, lung, skin, melanoma, colon, colorectal, rectal, prostate and bone cancer). 1,25(OH)$_2$D has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, chronic obstructive pulmonary disease, polycystic kidney disease (PKD), polycystic ovary syndrome, pancreatitis, nephritis, hepatitis, and/or infection. Vitamin D-responsive diseases have also been reported to include hypertension and cardiovascular diseases. Thus, the invention contemplates prophylactic or therapeutic treatment of subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

The present invention is further explained by the following example which should not be construed by way of limiting the scope of the present invention. The following example demonstrates that the concomitant administration of Vitamin D repletion and Vitamin D hormone replacement therapies has improved efficacy in reducing or preventing elevated blood PTH levels as well as maintaining adequate and appropriate levels of serum calcium, serum phosphorous, serum total 25-hydroxyvitamin D and serum total 1,25-dihydroxyvitamin D.

EXAMPLE 1

Efficacy Study in Patients With Stage 4 CKD and Secondary Hyperparathyroidism Associated With Vitamin D Insufficiency The effectiveness of 25-hydroxyvitamin $D_3$ and, as necessary, 1,25-dihydroxyvitamin $D_2$ in restoring serum total 25-hydroxyvitamin D to optimal levels (>30 ng/mL) and serum total 1,25-dihydroxyvitamin D to adequate levels (>25 pg/mL) is examined in an open-ended study of adult male and female patients with Stage 4 CKD and secondary hyperparathyroidism associated with vitamin D insufficiency. Two formulations are used in the study. One of the formulations (Formulation #1) is a soft gelatin capsule containing 30 μg of 25-hydroxyvitamin $D_3$. The second formulation (Formulation #2) is a soft gelatin capsule containing 0.25 μg of 1,25-dihydroxyvitamin $D_2$. A total of 100 subjects participate in this study, all of whom are aged 30 to 70 years and have serum 25-hydoxyvitamin D levels between 15 and 29 ng/mL (inclusive) and serum intact parathyroid hormone (iPTH) levels above the target levels published in the current K/DOQI Guidelines at the time of enrolment. All subjects abstain from taking other Vitamin D supplements for 60 days before study start and continuing through study termination, and from significant sun exposure. All subjects begin daily dosing with two capsules of Formulation #1. Serum total 25-hydroxyvitamin D is measured at biweekly intervals and serum iPTH is determined at quarterly intervals. After 1 month, the daily dosage of Formulation #1 is maintained unchanged in patients whose serum total 25-hydroxyvitamin D is between 50 and 90 ng/mL, increased by one capsule in patients whose serum total 25-hydroxyvitamin D is below 50 ng/mL, and decreased by one capsule per day in patients whose serum total 25-hydroxyvitamin D is above 90 ng/mL. Further adjustments in the daily dose are made as needed in order to maintain serum total 25-hydroxyvitamin D between 50 and 90 ng/mL. After 6 months, subjects whose serum iPTH levels are above K/DOQI targets also begin receiving a daily dose of one capsule of Formulation #2. The dosage of Formulation #2 is adjusted upwards in one capsule increments at monthly intervals until serum iPTH levels are lowered progressively into K/DOQI targets. Dosing with both Formulation #1 and #2 is continued indefinitely, provided that hypercalcemia, hypercalciuria and hyperphosphatemia do not develop, in which case appropriate adjustments in dosage are made. After 1 year, the subjects' ongoing serum total 25-hydroxyvitamin D levels are found to remain stable between 50 and 90 ng/mL, serum total 1,25-dihydroxyvitamin D levels are found to remain stable at levels that are within the subjects' normal historical range prior to the onset of advanced CKD and serum iPTH is found to remain stable at levels consistent with targets published in the K/DOQI Guidelines. The incidence of hypercalcemia, hypercalciuria and hyperphosphatemia are rare once stable dosing has been achieved.

All patents, publications and references cited herein are hereby fully incorporated by reference. In case of conflict between the present disclosure and incorporated patents, publications and references, the present disclosure should control.

Embodiments contemplated in view of the foregoing description include the following numbered paragraphs.

1. A method of treating and preventing secondary hyperparathyroidism in a patient suffering from chronic kidney disease, comprising increasing or maintaining blood concentrations of both 25-hydroxyvitamin D and 1,25-dihydroxyvitamin D in the patient by administering 25-hydroxyvitamin $D_3$ and optionally 25-hydroxyvitamin $D_2$, wherein 25-hydroxyvitamin $D_3$ is the predominant prohormone in circulation.

2. The method of paragraph 1, comprising administering said 25-hydroxyvitamin D compounds such that blood concentrations of 25-hydroxyvitamin D are increased to and maintained at or above 30 ng/mL.

3. The method according to paragraph 1, further comprising administering 1,25-dihydroxyvitamin $D_2$ as a Vitamin D hormone replacement therapy to the patient.

4. The method of paragraph 3, comprising administering the 1,25-dihydroxyvitamin $D_2$ as such that blood concentrations of serum total 1,25-dihydroxyvitamin $D_2$ are increased to or maintained within a patient's normal historical physiological range for serum total 1,25-dihydroxyvitamin D without causing side effects, including hypercalcemia, hyperphosphatemia, hypercalciuria and oversuppression of iPTH.

5. A method of concurrently lowering or maintaining plasma iPTH levels, increasing or maintaining serum calcium levels, maintaining serum phosphorous levels, increasing or maintaining serum 25-hydroxyvitamin D, or increasing or maintaining serum 1,25-dihydroxyvitamin D levels in a human patient diagnosed with early stage CKD, comprising administering to the patient, 25-hydroxyvitamin $D_3$ and optionally 25-hydroxyvitamin D$_2$ and, further optionally as necessary, 1,25-dihydroxyvitamin D$_2$, such that the blood concentrations of 25-hydroxyvitamin D in the patient are increased to and maintained at or above 30 ng/mL, with 25-hydoxyvitamin D$_3$ being the predominant prohormone, and blood concentrations of 1,25-dihydroxyvitamin D are increased to or maintained within a patient's normal historical physiological range for 1,25-dihydroxyvitamin D.

6. A method of reducing the risk of over suppression of plasma iPTH levels in a patient undergoing treatment for elevated levels of plasma iPTH, or maintenance/prevention therapy for secondary hyperparathyroidism, comprising administering 25-hydroxyvitamin D$_3$ and optionally 25-hydroxyvitamin D$_2$ and, further optionally as necessary, 1,25-dihydroxyvitamin D$_2$, so that the blood concentrations of 25-hydroxyvitamin D are increased to and maintained at or above 30 ng/mL, with 25-hydroxyvitamin D$_3$ being the predominant prohormone, and blood concentrations of 1,25-dihydroxyvitamin D are increased to or maintained within a patient's normal historical physiological range for 1,25-dihydroxyvitamin D, and elevated plasma iPTH levels are decreased or controlled while avoiding an abnormally low bone turnover rate.

7. A method of treatment, comprising proactively administering 25-hydroxyvitamin D$_3$ and/or Vitamin D$_3$, optionally concurrently with administration of 25-hydroxyvitamin D$_2$, and/or Vitamin D$_2$, to an early stage CKD patient having the potential to develop secondary hyperparathyroidism due to Vitamin D insufficiency or deficiency.

8. A method according to paragraph 4, comprising administering said 25-hydroxyvitamin D$_3$ to increase blood concentration of 25-hydroxyvitamin D in the patient to a level of at least 30 ng/mL.

9. The method according to paragraph 8, further comprising administering said 25-hydroxyvitamin D$_3$ to maintain blood concentration of 25-hydroxyvitamin D in the patient at a level of at least 30 ng/mL for at least 30 days.

10. The method according to paragraph 9, comprising administering said 25-hydroxyvitamin D$_3$ to maintain blood concentration of 25-hydroxyvitamin D in the patient at a level of at least 30 ng/mL for at least 90 days.

11. The method according to paragraph 2, further comprising administering said 25-hydroxyvitamin D$_3$ to maintain blood concentration of 25-hydroxyvitamin D in the patient at a level of at least 30 ng/mL for at least 30 days.

12. The method according to paragraph 11, comprising administering said 25-hydroxyvitamin D$_3$ to maintain blood concentration of 25-hydroxyvitamin D in the patient at a level of at least 30 ng/mL for at least 90 days.

13. The method according to paragraph 5, further comprising administering said 25-hydroxyvitamin D$_3$ to maintain blood concentration of 25-hydroxyvitamin D in the patient at a level of at least 30 ng/mL for at least 30 days.

14. The method according to paragraph 13, comprising administering said 25-hydroxyvitamin D$_3$ to maintain blood concentration of 25-hydroxyvitamin D in the patient at a level of at least 30 ng/mL for at least 90 days.

15. The method according to paragraph 6, further comprising administering said 25-hydroxyvitamin D$_3$ to maintain blood concentration of 25-hydroxyvitamin D in the patient at a level of at least 30 ng/mL for at least 30 days.

16. The method according to paragraph 15, comprising administering said 25-hydroxyvitamin D$_3$ to maintain blood concentration of 25-hydroxyvitamin D in the patient at a level of at least 30 ng/mL for at least 90 days.

17. A method according to paragraph 7, comprising administering said 25-hydroxyvitamin D$_3$ to increase blood concentration of 25-hydroxyvitamin D in the patient to a level of at least 30 ng/mL.

18. The method according to paragraph 17, further comprising administering said 25-hydroxyvitamin D$_3$ to maintain blood concentration of 25-hydroxyvitamin D in the patient at a level of at least 30 ng/mL for at least 30 days.

19. The method according to paragraph 18, comprising administering said 25-hydroxyvitamin D$_3$ to maintain blood concentration of 25-hydroxyvitamin D in the patient at a level of at least 30 ng/mL for at least 90 days.

20. The method according to paragraph 7, comprising administering 25-hydroxyvitamin D$_3$ such that 25-hydroxyvitamin D$_3$ is the predominant prohormone in circulation.

What is claimed is:

1. A method of treating secondary hyperparathyroidism in a patient suffering from chronic kidney disease, comprising administering a sustained release composition comprising 25-hydroxyvitamin D$_3$ and optionally D$_2$ to increase or maintain blood concentrations of both 25-hydroxyvitamin D and 1,25-dihydroxyvitamin D in the patient, wherein 25-hydroxyvitamin D$_3$ is the predominant prohormone in circulation, wherein the patient is receiving one or more medications that increase the catabolism of vitamin D, or one or more medications that reduce absorption of vitamin D, or one or more medications that inhibit activation of vitamin D, or one or more medications that decrease calcium absorption, or any combination of the foregoing.

2. The method of claim 1, wherein the patient is receiving phenytoin, or fosphenytoin, or phenobarbital, or carbamazepine, or rifampin.

3. The method of claim 2, wherein the patient is receiving phenytoin.

4. The method of claim 2, wherein the patient is receiving fosphenytoin.

5. The method of claim 2, wherein the patient is receiving phenobarbital.

6. The method of claim 2, wherein the patient is receiving carbamazepine.

7. The method of claim 2, wherein the patient is receiving rifampin.

8. The method of claim 1, wherein the patient is receiving cholestyramine, or colestipol, or orlistat, or a fat substitute.

9. The method of claim 8, wherein the patient is receiving cholestyramine.

10. The method of claim 9, wherein the patient suffers from obesity.

11. The method of claim 10, wherein the patient has CKD Stage 3 or 4.

12. The method of claim 8, wherein the patient is receiving colestipol.

13. The method of claim 8, wherein the patient is receiving orlistat.

14. The method of claim 8, wherein the patient is receiving a fat substitute.

15. The method of claim 8, wherein the patient suffers from obesity.

16. The method of claim 1, wherein the patient is receiving one or more medications that inhibit activation of vitamin D.

17. The method of claim 16, wherein the patient is receiving ketoconazole.

18. The method of claim 1, wherein the patient is receiving one or more medications that decrease calcium absorption.

19. The method of claim 18, wherein the patient is receiving a corticosteroid.

20. The method of claim 1, wherein the patient suffers from obesity.

21. The method of claim 1, wherein the sustained release composition comprising 25-hydroxyvitamin $D_3$ and optionally $D_2$ comprises a soft gelatin capsule.

22. The method of claim 1, wherein the patient is receiving one or more medications that increase the catabolism of vitamin D.

23. The method of claim 1, wherein the patient is receiving one or more medications that reduce absorption of vitamin D.

24. A method of treating secondary hyperparathyroidism in a patient suffering from chronic kidney disease, comprising administering a sustained release composition comprising 25-hydroxyvitamin $D_3$ and optionally 25-hydroxyvitamin $D_2$ to increase or maintain blood concentrations of both 25-hydroxyvitamin D and 1,25-dihydroxyvitamin D in the patient, wherein 25-hydroxyvitamin $D_3$ is the predominant prohormone in circulation, in a patient receiving a medication that increases the catabolism of vitamin D, or a medication that reduce absorption of vitamin D, or a medication that inhibits activation of vitamin D, or a medication that decreases calcium absorption.

25. The method of claim 24, wherein the patient is receiving phenytoin, fosphenytoin, phenobarbital, carbamazepine, rifampin, cholestyramine, colestipol, orlistat, ketoconazole, or a corticosteroid.

26. The method of claim 25, wherein the sustained release composition comprising 25-hydroxyvitamin $D_3$ and optionally 25-hydroxyvitamin $D_2$ comprises a soft gelatin capsule.

\* \* \* \* \*